(12) United States Patent
Maher

(10) Patent No.: US 7,897,637 B2
(45) Date of Patent: Mar. 1, 2011

(54) METHODS OF USING FLAVONOIDS TO ENHANCE MEMORY

(75) Inventor: Pamela A. Maher, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 101 days.

(21) Appl. No.: 11/780,350

(22) Filed: Jul. 19, 2007

(65) Prior Publication Data

US 2008/0021096 A1    Jan. 24, 2008

Related U.S. Application Data

(60) Provisional application No. 60/807,805, filed on Jul. 19, 2006.

(51) Int. Cl.
  *A01N 43/16*  (2006.01)
  *A61K 31/35*  (2006.01)
  *C07D 311/00* (2006.01)
(52) U.S. Cl. ......................... 514/456; 549/403
(58) Field of Classification Search ................. 514/456; 549/403
  See application file for complete search history.

(56) References Cited

U.S. PATENT DOCUMENTS

| | | | |
|---|---|---|---|
| 4,591,600 | A | 5/1986 | Creuzet et al. |
| 2001/0047032 | A1 | 11/2001 | Castillo et al. |
| 2003/0194453 | A1 | 10/2003 | Coleman et al. |
| 2004/0132671 | A1 | 7/2004 | Zhao et al. |
| 2005/0004046 | A1 | 1/2005 | Praag et al. |
| 2006/0111307 | A1 | 5/2006 | Robbins |

FOREIGN PATENT DOCUMENTS

| | | |
|---|---|---|
| WO | WO 01/49281 A2 | 7/2001 |
| WO | WO 2005/004814 A2 | 1/2005 |
| WO | WO 2005/020932 A2 | 3/2005 |
| WO | WO 2006/043752 A1 | 4/2006 |
| WO | WO 2006/076681 A2 | 7/2006 |
| WO | WO 2006/138418 A2 | 12/2006 |
| WO | WO 2007/102861 A2 | 9/2007 |

OTHER PUBLICATIONS

Anekonda et al. Journal of Neurochemistry, 2006 (but published online Oct. 7, 2005), vol. 96, pp. 305-313.*

Vippagunta et al. Advanced Drug Delivery Reviews. 2001. vol. 48, pp. 3-26.*

Ishige et al., "Flavonoids Protect Neuronal Cells from Oxidative Stress by Three Distinct Mechanisms," *Free Radic. Biol. Med.* 30:433-446, 2001.

Mahar et al., "Flanovoid Fisetin Promotes ERK-Dependent Long-Term Potentiation and Enhances Memory," *PNAS* 103:16568-16573, 2006.

Singh et al., "Free Radicals and Oxidative Stress in Neurodegenerative Diseases: Relevance of Dietary Antioxidants," *JIACM* 5:218-225, 2004.

USDA Report, "USDA Database for the Flavonoid Content of Selected Foods," prepared by Nutrient Data Laboratory, Food Composition Laboratory, Beltsville Human Nutrition Research Center, Agricultural Research Service, and U.S. Department of Agriculture, Baltimore, MD, Mar. 2003.

Žerovnik, "Amyloid-Fibril Formation—Proposed Mechanisms and Relevance to Conformational Disease," *Eur. J. Biochem.* 269:3362-3371, 2002.

Dajas et al., "Cell Culture Protection and in vivo Neuroprotective Capacity of Flavonoids," *Neurotox. Res.* 5:425-432, 2003.

Maher, "A Comparison of the Neurotrophic Activities of the Flavonoid Fisetin and Some of its Derivatives," *Free Radic. Res.* 40:1105-1111, 2006.

Rivera et al., "Some Aspects of the in vivo Neuroprotective Capacity of Flavonoids: Bioavailability and Structure-Activity Relationship," *Neurotox. Res.* 6:543-553, 2004.

Sagara et al., "Induction of PC12 Cell Differentiation by Flavonoids is Dependent Upon Extracellular Signal-Regulated Kinase Activation," *J. Neurochem.* 90:1144-1155, 2004.

Shen et al., "Pathogenesis of Neurodegenerative Diseases and the Effect of Natural Products on Nitric Oxide Production Implicating in These Diseases," *J. Chin. Med.* 16:63-87, 2005.

van Praag et al., "Plant-Derived Flavanol (—) Epicatechin Enhances Angiogenesis and Retention of Spatial Memory in Mice," *J. Neurosci.* 27:5869-5878, 2007.

van Praag, Henriette, "Exercise and the Brain: Something to Chew On," *Trends Neurosci.* 32:283-290, 2009.

* cited by examiner

*Primary Examiner* — Sreeni Padmanabhan
*Assistant Examiner* — Samira Jean-Louis
(74) *Attorney, Agent, or Firm* — Klarquist Sparkman, LLP

(57) ABSTRACT

Described herein are flavonoids (e.g., 5-desoxy flavones and/or 5-desoxy flavonols, including without limitation fisetin and its derivatives) that activate ERK and induce CREB phosphorylation in neuronal cultures, facilitate long-term potentiation in hippocampal slices and enhance object recognition in vivo. Methods of using these flavonoids, for instance, for enhancing memory are described.

38 Claims, 12 Drawing Sheets

A

B

A.

B.

C.

D.

METHODS OF USING FLAVONOIDS TO ENHANCE MEMORY

CROSS-REFERENCE TO RELATED APPLICATION

This application claims the benefit of U.S. Provisional Application No. 60/807,805 filed Jul. 19, 2006, herein incorporated by reference.

STATEMENT OF GOVERNMENT SUPPORT

This invention was made with United States government support pursuant to grant no. NS28121 from the U.S. Public Health Service, the United States government has certain rights in the invention.

FIELD

This disclosure concerns the use of 5-desoxy-flavones and 5-desoxy-flavonols, such as fisetin and/or its derivatives, to enhance memory in vivo and/or to promote nerve cell differentiation and/or protect nerve cells from oxidative damage.

BACKGROUND

Memory is the recollection of past experiences. Almost everyone forgets something occasionally and, typically, forgetfulness increases as a person grows older. Normal aging also may result in trouble learning new material or requiring longer time to recall learned material. Age-associated memory impairments are currently estimated to affect at least 16% of everyone over the age of 50 (Tully et al., *Nature Rev. Drug Discov.*, 2:267-277, 2003). Mild memory loss, while a nuisance, does not usually affect a person's normal day-to-day functioning. Other forms of memory loss can be more severe and have a functional impact. Common causes of memory loss of various severities include, among others, aging, Alzheimer's disease, neurodegenerative illness, head trauma or injury, seizures, general anesthetics (such as halothane, isoflurane, and fentanyl), alcoholism, stroke or transient ischemic attack (TIA), transient global amnesia, drugs (such as barbiturates or benzodiazepines), electroconvulsive therapy (especially if prolonged), temporal lobe brain surgery, brain masses (caused by tumors or infection), herpes encephalitis or other brain infections, and/or depression.

Long term potentiation (LTP) is considered to be the cellular basis of learning and memory and is dependent on synaptic plasticity (Bliss and Collingridge, *Nature*, 361:31-39, 1993), which can be defined as the long-lasting strengthening of the connections between two nerve cells. Synaptic plasticity in turn is believed to be dependent on a complex interplay of protein kinases, phosphatases, and transcription factors that ultimately give rise to long-term changes in the connections between nerve cells (Gaiarsa et al., *Trends Neurosci.* 25:564-570, 2002). Put more simply, a particular experience is registered in the brain as a circuit-specific pattern of neural activity and, due to synaptic plasticity, the structure of the circuit is modified so as to form a memory.

LTP was originally discovered in the hippocampus but has since been observed in other regions of the brain including the cerebral cortex, cerebellum and amygdala (Malenka and Bear, *Neuron*, 44:5-21, 2004). One model of learning postulates that the hippocampus is the gateway to long-term memory and, once the hippocampus has registered a memory, the memory is propagated to relevant portions of the cortex for storage (e.g., visual memory to visual cortex, auditory memory to auditory cortex, etc.) (for reviews, see, Tully et al., *Nature Rev. Drug Discov.*, 2:267-277, 2003; Adams and Sweatt, *Annu. Rev. Pharmacol. Toxicol.*, 42:135-163, 2002).

Neurotrophic factors, which modulate short- and long-term changes in neurons of the central nervous system (CNS), have been suggested to play roles in neuronal plasticity such as learning and memory (Lo, *Neuron*, 15:979-981, 1995; Thoenen, *Science*, 270:593-598, 1995). Neurotrophic factors support the survival, differentiation and functional maintenance of nerve cells. Because of these properties, neurotrophic factors have the potential to treat a variety of chronic and acute disorders of the CNS, including memory loss. However, many classical neurotrophic factors, such as nerve growth factor, are not well suited for therapeutic purposes due to their large size and proteinaceous nature (Levy et al., *BioDrugs*, 19:97-127, 2005). Thus, the identification of small molecules that can mimic some or all of the properties of neurotrophic factors could have great potential for treating CNS disorders, such as memory deficits.

Twenty eight different flavonoids, including representatives of all of the six different flavonoid classes (e.g., flavanones, flavan-3-ols, flavonols, flavones, anthocyanidins and isoflavones; U.S. Department of Agriculture, USDA database for the flavonoid content of selected foods, Beltsville, Md.:U.S. Department of Agriculture; 2003), were previously assayed for their ability to promote neurite outgrowth in PC12 cells (Sagara et al., *J. Neurochem.*, 90:1144-1155, 2004). Among the flavonoids tested, only four were found to promote PC12 cell differentiation and of these, fisetin (3,7,3',4',-tetrahydroxyflanone; a flavonol) was by far the most effective. Fisetin has an $EC_{50}$ for differentiation of 5 µM and at 10 µM routinely induces the differentiation of 75-80% of the cells The other three flavonoids that induced differentiation of PC12 cells, luteolin (5,7,3',4'-tetrahydroxyflavone; a flavone), quercetin (3,5,7,3',4'-pentahydroxyflavone; a flavonol) and isorhamnetin (3'-methoxy-3,5,7,4'-tetrahydroxyflavone; a flavonol), had $EC_{50}$s of 10 µM and at best induced the differentiation of only 50% of the cells.

The induction of differentiation by fisetin was dependent on the activation of the Ras-ERK cascade because inhibitors of this cascade blocked differentiation (Sagara et al., *J. Neurochem.*, 90:1144-1155, 2004). In addition to promoting nerve cell differentiation fisetin has also been shown to protect nerve cells from oxidative stress-induced death (Ishige et al., *Free Radic. Biol. Med.*, 30:433-446, 2001). However, the structural features of fisetin that underlie its functions of promoting nerve cell differentiation and/or protecting such cells from oxidative damage are unknown. Also unknown is whether the ability of fisetin to promote nerve cell differentiation and/or protect neural cells from oxidative damage have in vivo correlates.

A need exists for the identification of small molecules that can mimic some or all of the properties of neurotrophic factors. Such molecules have potential for treating CNS disorders, such as memory loss.

SUMMARY

Disclosed herein are fisetin derivatives that are surprisingly effective neurotrophic factors. These derivatives (including, for example, 3,3',4'-trihydroxyflavone and 3',4'-dihydroxyflavone) promote nerve cell differentiation and/or protect such cells from oxidative damage at significantly lower concentrations than does, for example, fisetin.

This disclosure also concerns the discovery that 5-desoxy-flavones and/or 5-desoxy-flavonols (such as fisetin and certain of its derivatives) improves memory in vivo. This important discovery enables, for instance, methods of enhancing memory in wide variety of subjects, including normal subjects or subjects suffering from memory loss.

Exemplary memory-enhancing 5-desoxy-flavones and/or 5-desoxy-flavonols are provided throughout the disclosure and, by way of example, include compounds having the following general structure:

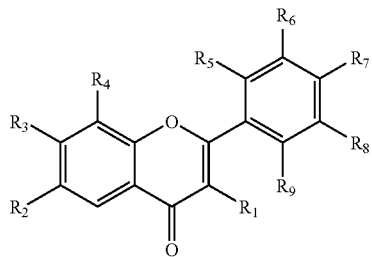

wherein $R_1$, $R_2$, $R_3$, $R_4$, $R_5$, $R_6$, $R_7$, $R_8$, and $R_9$ are independently hydrogen, alkyl, hydroxyl, acyl, or alkoxy; at least one of $R_6$ and $R_7$ is hydroxyl or acyl; and at least two of $R_1$, $R_3$, $R_6$, and $R_7$ are hydroxyl or acyl.

The foregoing and other features and advantages will become more apparent from the following detailed description of several embodiments, which proceeds with reference to the accompanying figures.

BRIEF DESCRIPTION OF THE FIGURES

FIG. 1A shows a time course of 3,3',4'-THF-induced ERK activation. FIG. 1B shows that fisetin and the indicated fisetin derivatives induce ERK activation and that PD98059 blocks such activation.

FIG. 4A shows that fisetin and some of its derivatives induced the expression of Nrf2 and HO-1. Similar results were obtained in 2-3 independent experiments. FIG. 4B shows treatment with PD98059 (as indicated) reduced Nrf2 and HO-1 induction by 3,7,4'-THF but had relatively no effect on the induction by fisetin or any of the other indicated derivatives.

In FIG. 5B, * indicates significantly different from control (P<0.01). In FIG. 5D, # indicates significantly different from control (P<0.01), and * indicates significantly different from fisetin alone (P<0.01). Similar results were obtained in 2-3 independent experiments.

In FIG. 10C, * indicates significantly different from control (P<0.005) (p42: 5 min: 1.68±0.06; 10 min: 1.31±0.05; 20 min: 1.42±0.03; p44: 5 min: 1.98±0.16; 10 min: 1.48±0.02; 20 min: 1.30±0.09; CREB: 5 min: 2.87±0.56; 10 min: 2.72±0.12; 20 min: 2.55±0.39). In FIG. 10D,* indicates significantly different from control (P<0.0005). # indicates significantly different from fisetin alone (P<0.0001). (p42: PD98059: 0.83±0.08; U0126: 0.30±0.05; 5 min fisetin: 1.68±0.06; fisetin+PD98059: 0.72±0.09; fisetin+U0126: 0.54±0.06; p44: PD98059: 0.75±0.5; U0126: 0.13±0.06; 5 min fisetin: 1.98±0.16; fisetin+PD98059: 0.701±0.10; fisetin+U0126: 0.29±0.05; CREB: PD98059: 0.64±0.11; U0126: 0.71±0.31; 5 min fisetin: 2.87±0.56; fisetin+PD98059: 0.55±0.05; fisetin+U0126: 0.20±0.03). Similar results were obtained in 2 independent experiments.

DETAILED DESCRIPTION

I. Introduction

Figure 1:
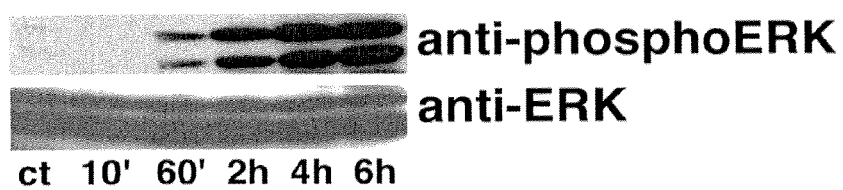
FIG. 1 shows reproductions of Western blots of cell extracts of PC12 cells untreated (ct or control) or treated with 3,3',4'-THF (FIG. 1A) or fisetin or the indicated fisetin derivative and, where indicated, the MEK inhibitor, PD98059 (FIG. 1B). The blots were probed with anti-phospho ERK or anti-ERK antibodies as indicated.
Figure 1:
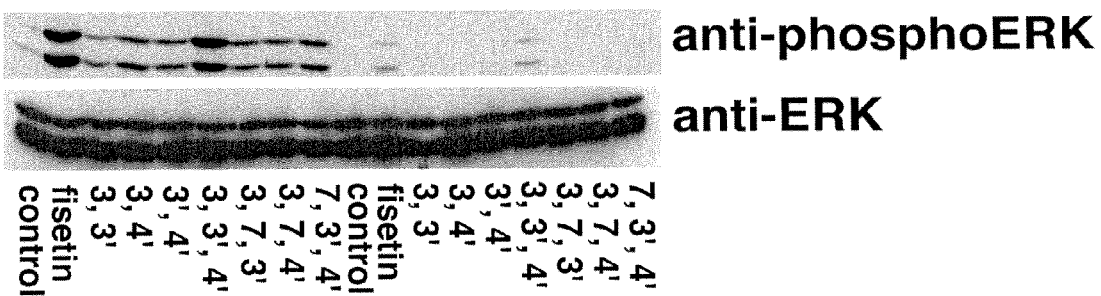

Disclosed herein are methods for enhancing memory in a subject. Such methods involve administering to a subject an effective amount (e.g., from about 50 mg to about 1000 mg) of a 5-desoxy-flavone or 5-desoxy-flavonol or a hydrate or pharmaceutically acceptable salt of either thereof. In some method embodiments, a 5-desoxy-flavone is a 5(H)-flavone and a 5-desoxy-flavonol is 5(H)-flavonol.

In other method embodiments, a 5-desoxy-flavone or the 5-desoxy-flavonol is a compound having the formula:

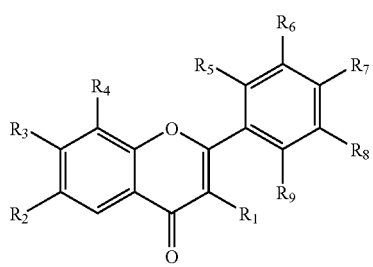

wherein $R_1$, $R_2$, $R_3$, $R_4$, $R_5$, $R_6$, $R_7$, $R_9$, and $R_9$ are independently hydrogen, alkyl, hydroxyl, acyl, acyloxy, alkoxy carbonyl or alkoxy; at least one of $R_6$ and $R_7$ is hydroxyl, acyl, or acyloxy; and at least two of $R_1$, $R_3$, $R_6$, and $R_7$ are hydroxyl, acyl, or acyloxy; or hydrate or a pharmaceutically acceptable salt thereof. In more particular examples, $R_1$, $R_2$, $R_3$, $R_4$, $R_5$, $R_6$, $R_7$, $R_8$, and $R_9$ are independently hydrogen, hydroxyl, acyl, alkoxy carbonyl or acyloxy. In other particular examples, $R_1$, $R_2$, $R_3$, $R_4$, $R_5$, $R_6$, $R_7$, $R_8$, and $R_9$ are independently hydrogen, hydroxyl, or acyl; at least one of $R_6$ and $R_7$ is hydroxyl, or acyloxy; mid at least two of $R_1$, $R_3$, $R_6$, and $R_7$ are hydroxyl, or acyloxy.

Some method embodiments involve a 5-desoxy-flavone or a 5-desoxy-flavonol having the formula:

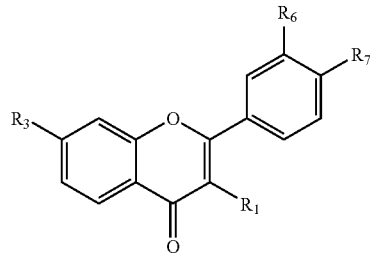

wherein $R_1$, $R_3$, $R_6$, and $R_7$ are independently hydrogen, alkyl, hydroxyl, acyl, acyloxy, alkoxy carbonyl or alkoxy; at least one of $R_6$ and $R_7$ is hydroxyl, acyl, alkoxy carbonyl or acyloxy; and at least two of $R_1$, $R_3$, $R_6$, and $R_7$ are hydroxyl, acyl, alkoxy carbonyl or acyloxy; or hydrate or a pharmaceutically acceptable salt thereof. In more particular embodiments, $R_1$, $R_3$, $R_6$, and $R_7$ are independently hydrogen, hydroxyl, acyl, alkoxy carbonyl or acyloxy. In other more particular embodiments, $R_1$, $R_3$, $R_6$, and $R_7$ are independently hydrogen, hydroxyl, or acyl; at least one of $R_6$ and $R_7$ is hydroxyl, or acyloxy; and at least two of $R_1$, $R_3$, $R_6$, and $R_7$ are hydroxyl, or acyloxy.

In certain method embodiments involving compounds of either of the foregoing formulas, $R_6$ is hydroxyl, or $R_7$ is hydroxyl, or $R_6$ and $R_7$ are hydroxyl, or $R_1$ and $R_6$ are hydroxyl, or $R_1$ and $R_7$ are hydroxyl, or $R_1$, $R_6$, and $R_7$ are hydroxyl, or $R_3$, $R_6$, and $R_7$ are hydroxyl, or $R_1$, $R_3$, and $R_6$, are hydroxyl, or $R_1$, and $R_3$, and $R_7$ are hydroxyl. In other method embodiments involving compounds of either of the foregoing formulas, alkoxy is lower alkoxy (such as methoxy), and/or acyloxy is lower acyloxy, and/or alkyl is lower alkyl (such as methyl or ethyl).

Compounds useful in some disclosed method embodiments include 3,3',4',7-tetrahydroxyflavone (fisetin), 3,3',4'-trihydroxyflavone, 3',4',7-trihydroxyflavone, 3,3',7-trihydroxyflavone, 3,4',7-trihydroxyflavone, 3,3'-dihydroxyflavone, 3,4'-dihydroxyflavone, and/or 3',4'-dihydroxyflavone. In particular method embodiments, useful compounds include 3,3',4',7-tetrahydroxyflavone (fisetin), 3,3',4'-trihydroxyflavone, and/or 3,4',7-trihydroxyflavone.

Some method embodiments exclude the use of 3,3',4',7-tetrahydroxyflavone (fisetin). Other method embodiments involve a subject that does not have amyloidosis or a disease characterized by α-synuclein fibril formation. Still other method embodiments involve a normal subject.

Further disclosed herein are uses of any of the above-described 5-desoxy-flavones and/or 5-desoxy-flavonols and/or a hydrate or pharmaceutically acceptable salt of either thereof in the manufacture of a medicament for the enhancement of memory.

II. Abbreviations and Terms

ARE antioxidant response element
BSO buthionine sulfoximine
DHF dihydroxyflavone
fEPSPs evoked field excitatory postsynaptic potentials
GSH glutathione
HO-1 heme oxygenase-1
LTP long-term potentiation
Nrf2 NF-E2-related factor 2
ROS reactive oxygen species
TEAC Trolox Equivalent Activity Concentration THF trihydroxyflavone Unless otherwise noted, technical terms are used according to conventional usage.

Definitions of common terms in chemistry may be found in *The McGraw-Hill Dictionary of Chemical Terms*, Second Edition, New York:McGraw-Hill, 2003, and Dean, *Lange's Handbook of Chemistry*, Fifteenth Edition, New York: McGraw-Hill, 1999; Halliwell and Gutteridge, *Free Radicals in Biology and Medicine*, Third Edition, Oxford: Oxford University Press, 2000.

In order to facilitate review of the various embodiments of the invention, the following explanations of specific terms are provided:

"Acyl" refers to a group having the structure —C(O)R, where R may be alkyl or substituted alkyl. "Lower acyl" groups are those that contain from 1 to 10 (such as from 1 to 6) carbon atoms.

"Acyloxy" refers to a group having the structure —OC(O)R, where R may be optionally substituted alkyl or optionally substituted aryl. "Lower acyloxy" groups are those where R contains from 1 to 10 (such as from 1 to 6) carbon atoms.

"Alkoxy" refers to a group having the formula —OR, wherein R is an alkyl group "Lower alkoxy" refers to an —OR group in which the R group has from 1 to 10 carbon atoms, such as from 1 to 6 carbon atoms. Examples of lower alkoxy groups include, but are not limited to, methoxy, ethoxy, n-propoxy, isopropoxy and butoxy groups.

"Alkoxy carbonyl" refers to a group of the formula —C(O)OR, where R may be optionally substituted alkyl or optionally substituted aryl. "Lower alkoxy carbonyl" groups are those where R contains from 1 to 10 (such as from 1 to 6) carbon atoms.

"Alkyl" refers to a straight-chain, branched-chain, or cyclic hydrocarbon, which is saturated. This term is further exemplified by groups such as methyl, ethyl, n-propyl, isopropyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

In some examples, an alkyl group contains from 1 to 25 carbon atoms, unless a different number of carbon atoms is expressly stated. The term "lower alkyl" refers to an alkyl group having from 1 to 10 carbon atoms (such as from 1 to 6 carbon atoms). This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl. Particular examples of lower alkyls are methyl, butyl and propyl (including isopropyl).

Flavone: A Compound having the Base Structure:

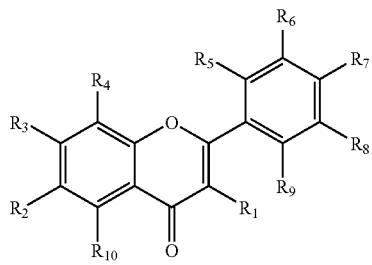

where any one or more of the $R_1$, $R_2$, $R_3$, $R_4$, $R_5$, $R_6$, $R_7$, $R_8$, $R_9$, or $R_{10}$ independently are hydrogen, alkyl (such as lower alkyl, e.g., methyl or ethyl), hydroxyl, or a substituent that may be metabolized in vivo to a hydroxyl group (e.g., acyl, acyloxy, and/or alkoxy). A flavone where $R_{10}$ is not a hydroxyl group is referred to as a "5-desoxy-flavone." A flavone where $R_{10}$ is hydrogen is referred to as a "5(H)-flavone."

A 3-hydroxy flavone (where $R_1$ is hydroxyl) is more particularly referred to as a "flavonol." Accordingly, a flavonol has the base structure:

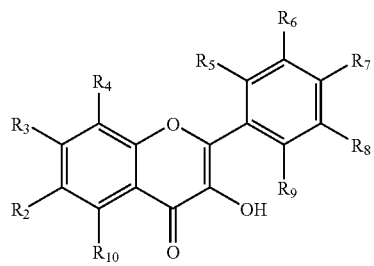

where $R_1$, $R_2$, $R_5$, $R_6$, $R_7$, $R_8$, $R_9$, or $R_{10}$ are as described for a flavone. A flavonol where $R_{10}$ is not a hydroxyl group is referred to as a "5-desoxy-flavonol." A flavonol where $R_{10}$ is hydrogen is referred to as a "5(H)-flavonol."

Treating or treatment: With respect to an impairment or disorder (such as memory loss), either term includes (i) preventing the impairment or disorder, e.g., causing the clinical symptoms of the impairment or disorder not to develop in a subject who does not yet experience or display symptoms of the impairment or disorder, (ii) inhibiting the impairment or disorder, e.g., arresting the development of the impairment or disorder or its clinical symptoms, or (iii) relieving the impairment or disorder, e.g., causing regression of the impairment or disorder or its clinical symptoms.

Compounds that have the same molecular formula but differ in the nature or sequence of bonding of their atoms or the arrangement of their atoms in space are termed "isomers" Isomers that differ in the arrangement of their atoms in space are termed "stereoisomers". Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture."

The compounds described herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, New York: John Wiley and Sons, 1992, Chapter 4).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A or B", or "including A and B."

Materials, methods, and examples are illustrative only and not intended to be limiting. Methods and materials similar or equivalent to those described herein can be used in the practice or testing of the present invention. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978; Sambrook et *Molecular Cloning: A Laboratory Manual*, 2d ed., Cold Spring Harbor Laboratory Press, 1989; Sambrook et al. *Molecular Cloning: A Laboratory Manual*, 3d ed. Cold Spring Harbor Press, 2001; Ausubel et al., *Current Protocols in Molecular Biology*, Greene Publishing Associates, 1992 (and Supplements to 2000); Ausubel et al., *Short Protocols ion Molecular Biology: A Compendium aft Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies. A Laboratory Manual*, Cold Spring Harbor Laboratory Press, 1999.

III. Compounds

Disclosed herein are methods for enhancing memory in a subject involving the administration to a subject of an effective amount of a 5-desoxy-flavone, a 5-desoxy-flavonol, hydrates and/or pharmaceutically acceptable salts of either, or combinations of any thereof. In some embodiments, a 5-desoxy-flavone is a 5(H)-flavone and/or a 5-desoxy-flavonol is a 5(H)-flavonol. Particular embodiments have the structures described in more detail below. In the structures that follow, all valency requirements are understood to be satisfied. Thus, for example, carbon atoms have four bonds to other atoms, even if all such bonds are not shown. Where all four bonds to a carbon atom are not shown, additional bonds to hydrogen atoms are implied.

A. Structures

Some exemplary flavonoids (e.g., 5-desoxy-flavones and/or 5-desoxy-flavonols) useful in the disclosed methods have the formula:

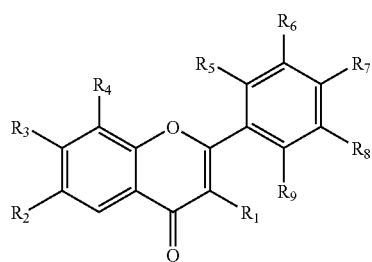

Formula I wherein $R_1$, $R_2$, $R_3$, $R_4$, $R_5$, $R_6$, $R_7$, $R_8$, and $R_9$ are independently hydrogen, alkyl (such as lower alkyl, eg., methyl or ethyl), hydroxyl, or a substituent that may be substantially cleaved in vivo to yield a hydroxy group (for example, by hydrolysis and/or by the action of one or more endogenous esterases); at least one of $R_6$ and $R_7$ is hydroxyl or a substituent that may be substantially cleaved in vivo to a yield a hydroxy group; and at least two of $R_1$, $R_3$, $R_6$, and $R_7$ are hydroxyl or a substituent that may be substantially cleaved in vivo to a hydroxy group. Examples of suitable groups for $R_{1-9}$ that can be cleaved in vivo to provide a hydroxy group include, without limitation, acyl, acyloxy and alkoxy carbonyl groups. Compounds having such cleavable groups are referred to as "prodrugs." The term "prodrug," as used herein, means a compound of Formula I which includes a substituent that is convertible in vivo (e.g. by hydrolysis) to a hydroxyl group. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). Design and Application of Prodrugs, Textbook of Drug Design and Development, Chapter 5, 113 191 (1991), Bundgaard, et al., Journal of Drug Deliver Reviews, 8:1 38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

In particular examples, $R_1$, $R_2$, $R_3$, $R_4$, $R_5$, $R_6$, $R_7$, $R_8$, and $R_9$ are independently hydrogen, alkyl (such as lower alkyl, e.g., methyl or ethyl), hydroxyl, for example acyloxy (such as lower acyloxy, for example acetyl or benzoyl), or alkoxy (such as lower alkoxy, e.g., methoxy); at least one of $R_6$ and $R_7$ is hydroxyl, acyl (such as lower acyl), or acyloxy (such as lower acyloxy); and at least two of $R_1$, $R_3$, $R_6$, and $R_7$ are hydroxyl, acyl (such as lower acyl), or acyloxy (such as lower acyloxy).

Other method embodiments involve compounds of Formula I, wherein $R_1$, $R_2$, $R_3$, $R_4$, $R_5$, $R_6$, $R_7$, $R_8$, and $R_9$ are independently hydrogen, hydroxyl, or acyl (such as lower acyl); at least one of $R_6$ and $R_7$ is hydroxyl or acyl (such as lower acyl); and at least two of $R_1$, $R_3$, $R_6$, and $R_7$ are hydroxyl or acyl (such as lower acyl). In some such embodiments, the substituent(s) indicated in Table I is (are each) hydroxyl and all other substituents are as described in this paragraph.

In more particular examples, $R_1$, $R_2$, $R_3$, $R_4$, $R_5$, $R_6$, $R_7$, $R_8$, and $R_9$ are independently hydrogen, hydroxyl, or acyl (such as lower acyl); at least one of $R_6$ and $R_7$ is hydroxyl; and at least two of $R_1$, $R_3$, $R_6$, and $R_7$ are hydroxyl. In some such examples the substituent(s) indicated in Table I is (are each) hydroxyl and all other substituents are as described in this paragraph.

Particular exemplary compounds having the structure of Formula I include compounds represented by Formula II:

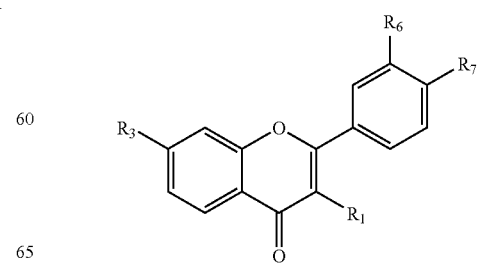

Formula II wherein $R_1$, $R_3$, $R_6$, and $R_7$ are independently hydrogen, alkyl (such as lower alkyl, e.g., methyl or ethyl), hydroxyl, or a substituent that may be substantially metabolized in vivo to a hydroxyl group; at least one of $R_6$ and $R_7$ is hydroxyl or a substituent that may be substantially metabolized in vivo to a hydroxyl group; and at least two of $R_1$, $R_3$, $R_6$, and $R_7$ are hydroxyl or a substituent that may be substantially metabolized in vivo to a hydroxyl group.

In particular examples, $R_1$, $R_3$, $R_6$, and $R_7$ are independently hydrogen, alkyl (such as lower alkyl, e.g., methyl or ethyl), hydroxyl, acyl (such as lower acyl), acyloxy (such as lower acyloxy), or alkoxy (such as lower alkoxy, e.g., methoxy); at least one of $R_6$ and $R_7$ is hydroxyl, acyl (such as lower acyl), or acyloxy (such as lower acyloxy); and at least two of $R_1$, $R_3$, $R_6$, and $R_7$ are hydroxyl, acyl (such as lower acyl), or acyloxy (such as lower acyloxy).

In more particular examples, $R_1$, $R_3$, $R_6$, and $R_7$ are independently hydrogen, alkyl (such as lower alkyl, e.g., methyl or ethyl), hydroxyl, acyl (such as lower acyl), acyloxy (such as lower acyloxy), or alkoxy (such as lower alkoxy, e.g., methoxy); at least one of $R_6$ and $R_7$ is hydroxyl or acyl (such as lower acyl); at least two of $R_1$, $R_3$, $R_6$, and $R_7$ are hydroxyl or acyl (such as lower acyl).

In even more particular examples, $R_1$, $R_3$, $R_6$, and $R_7$ are independently hydrogen, hydroxyl, acyl (such as lower acyl), or acyloxy (such as lower acyloxy); at least one of $R_6$ and $R_7$ is hydroxyl, acyl (such as lower acyl), or acyloxy (such as lower acyloxy); at least two of $R_1$, $R_3$, $R_6$, and $R_7$ are hydroxyl, acyl (such as lower acyl), or acyloxy (such as lower acyloxy).

In still more particular examples, $R_1$, $R_3$, $R_6$, and $R_7$ are independently hydrogen, hydroxyl acyl (such as lower acyl), or acyloxy (such as lower acyloxy); at least one of $R_6$ and $R_7$ is hydroxyl; at least two of $R_1$, $R_3$, $R_6$, and $R_7$ are hydroxyl.

Exemplary compounds useful in a disclosed method have a structure according to Formula I or II with $R_1$, $R_3$, $R_6$ and $R_7$ are set forth below in Table 1 and the remaining substituents are as previously described.

TABLE 1

Exemplary $R_1$, $R_3$, $R_6$, and $R_7$ substituents for Formula I or II

| Example | $R_1$ | $R_3$ | $R_6$ | $R_7$ |
|---------|-------|-------|-------|-------|
| 1 | —H | —H | —OH | —H |
| 2 | —H | —H | —H | —OH |
| 3 | —H | —H | —OH | —OH |
| 4 | —OH | —H | —OH | —H |
| 5 | —OH | —H | —H | —OH |
| 6 | —OH | —H | —OH | —OH |
| 7 | —H | —OH | —OH | —OH |
| 8 | —OH | —OH | —OH | —H |
| 9 | —OH | —OH | —H | —OH |

In particular, 5-desoxy-flavones (also 5(H)-flavones) for use in a disclosed method include:

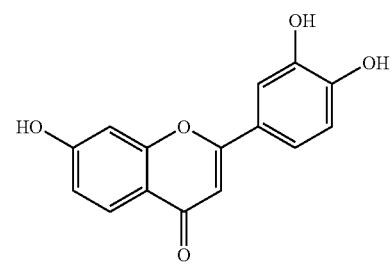

7,3',4'-trihydroxyflavone

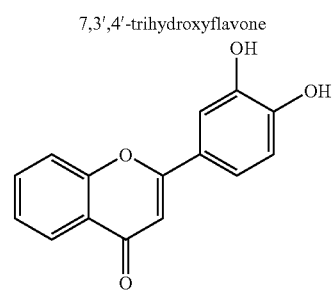

3',4'-trihydroxyflavone

Other 5-desoxyflavonols (also 5(H)-flavonols) for use in a disclosed method include:

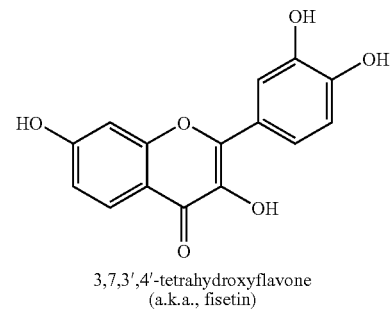

3,7,3',4'-tetrahydroxyflavone
(a.k.a., fisetin)

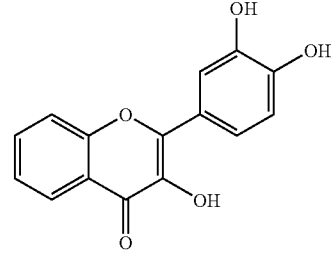

3,3',4'-trihydroxyflavone

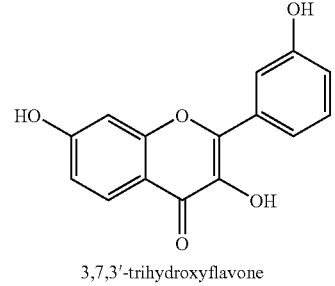

3,7,3'-trihydroxyflavone

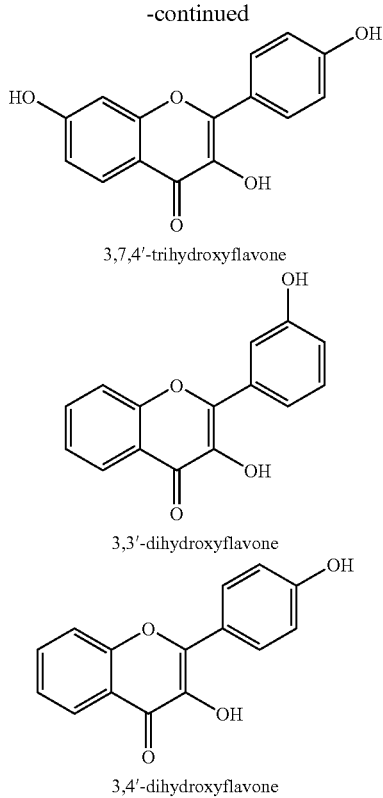

3,7,4'-trihydroxyflavone 3,3'-dihydroxyflavone 3,4'-dihydroxyflavone

Some method embodiments particularly involve the use of 3,3',4',7-tetrahydroxyflavone (fisetin), 3,3',4'-trihydroxyflavone, or 3,4',7-trihydroxyflavone. Other specific method embodiments employ 3,3',4'-trihydroxyflavone. In some methods, a compound to be administered is not 3,3',4',7-tetrahydroxyflavone (fisetin).

Particular method embodiments contemplate the use of solvates (such as hydrates), pharmaceutically acceptable salts and/or different physical forms of any of the herein described flavonoid compounds (e.g., 5-desoxy-flavones and/or 5-desoxy-flavonols).

1. Solvates, Salts and Physical Forms

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically-acceptable salts that are non-toxic. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements, In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, his- or tris-(2-hydroxy-lower alkyl)amines, such as mono-, his- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds such as ascorbic acid.

Additional counterions for forming pharmaceutically acceptable salts are found in *Remington's Pharmaceutical Sciences,* 17th Edition, Mack Publishing Company, Easton, Pa., 1985. A pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

2. Use for the Manufacture of a Medicament

Any of the above-described compounds (e.g., a 5-desoxy-flavone or a 5-desoxy-flavonol or a hydrate or pharmaceutically acceptable salt of either) or combinations thereof are intended for use in the manufacture of a medicament for the enhancement of memory in a subject. Formulations suitable for such medicaments, subjects who may benefit from same and other related features are described elsewhere herein.

B. Obtaining 5-Desoxy-Flavones and/or 5-Desoxy-Flavonols

In certain examples, one or more flavonoids useful in disclosed methods (such as fisetin and other 5-desoxy flavonols and/or 5-desoxy flavones) can be obtained from a variety of sources. Numerous commercial suppliers of flavonoids, including 3,3',4',7-tetrahydroxyflavone (fisetin), 3,3',4'-trihydroxyflavone, 3',4',7-trihydroxyflavone, 3,3',7-trihydroxyflavone, 3,4',7-trihydroxyflavone, 3,3'-dihydroxyflavone, 3,4'-dihydroxyflavone, or 3',4'-dihydroxyflavone, are available. Such suppliers including, for example, Alexis (San Diego, Calif., USA), Aldrich (Milwaukee, Wis., USA), CalBiochem (San Diego, Calif., USA), Indofine (Hillborough, N.J., USA).

Alternatively, 5-desoxy flavonols and/or 5-desoxy flavones (such as fisetin and its derivatives as described in Examples 1-13) are naturally occurring in, and can be isolated from, various plants. For example, fisetin and other flavones are found in *Rhus* sp. (e.g., sumac), *Fragaria* sp. (e.g., strawberry), *Allium* sp. (e.g., onion), *Solanum* sp. (e.g., tomato), *Nelumbo* sp. (e.g., lotus root), *Actinidia* sp. (e.g., kiwi fruit), *Prunus* sp. (e.g., peach), *Malus* sp (e.g., apple), *Cucumis* sp. (e.g., cucumber), *Diospyros* sp. (e.g., persimmunon) *Vitis* sp. (e.g., grape) (Chas et al., *Am. J. Botany,* 5(3):112-9, 1918; Arai et al., *J. Nutr.* 139:2243-50 2000).

Such plant-derived compositions can include extracts of plants or parts thereof which, optionally, can be processed physically and/or chemically during production of the composition to extract flavonoids from the plant and so increase and enrich the flavonoid content of the isolated composition. In some examples, plant materials containing flavonoids useful in a disclosed method can be isolated by fractionation. Fractionation methods are well known in the art and described, for example, in U.S. Pat. Nos. 4,428,876 and 5,702,752. Other widely known extraction processes, which can be used alone or in combination to isolated useful flavonoids from source material (such as, plants), include differential solubility, distillation, solvent extraction, adsorptive means, differential molecular filtration, precipitation, acetone extraction, silica gel adsorption chromatography (elution with 90:10 chloroform:methanol), and HPLC (see, e.g., Son et al., *Toxicol. Lett.,* 155:115-125, 2005).

The 5-desoxy flavonols and/or 5-desoxy flavones described above can be modified to produce derivatives, such as prodrugs. Methods for modifying such compounds are known to those of ordinary skill in the art of medicinal chemistry and include, for example, using acylating agents, such as an activated acid, for example an acid anhydride, halide or N-hydroxysuccinate to prepare an O-cyl flavone derivative. Similarly, one or more hydroxyl groups can be derivatized with alkoxy carbonyl groups to provide prodrug derivatives of flavone compounds. In certain, embodiments selective functionalization of a particular hydroxyl group to prepare a prodrug involves using a protected intermediate. Examples of suitable protecting group strategies and techniques for their implementation are known to those of ordinary skill in the art (see, Greene and Wuts, *Protective Groups in Organic Synthesis,* 3rd ed., New York: John Wiley & Sons, 1999).

C. Functional Assays

Flavonoid compounds (e.g., 5-desoxy flavones and/or 5-desoxy-flavonols) for use in the disclosed methods will have at least one function of a prototypical compound, such as fisetin or its derivatives as described in Examples 1-13. Assays suitable for establishing the usefulness of a described flavonoid (such as a 5-desoxy flavone, 5-desoxy-flavonol, 5(H)-flavone, or 5(H)-flavonol) in a disclosed method are known in the art and particular assays are provided below in the Examples. Briefly, such assays include (without limitation), for example, nerve cell (e.g. PC12) differentiation assay, assay for protection of nerve cells (e.g. PC12 or HT22 cells) from oxidative damage nerve cell (e.g., nerve cells in hippocampal slices) long-term potentiation assay, and/or cognitive function tests in a subject. In addition, some flavonoid compounds (eg., 5-desoxy flavones and/or 5-desoxy-flavonols) useful in the disclosed methods also may promote ERK and/or CREB activation (e.g., by phosphorylation) for instance, in PC12 cells and/or primary cortical neuron cultures (see, erg., Examples 2 and 5), V. Methods of Use Disclosed herein are methods of enhancing memory in a subject involving administering at least one 5-desoxy-flavone or 5-desoxy-flavonol or a hydrate or pharmaceutically acceptable salt of either thereof, each of which are described in detail elsewhere herein, (and, optionally, one or more other pharmaceutical agents) to a subject in an amount effective to enhance memory.

Disclosed methods can be used in any subject whose species is capable of forming memories (such as long-term memories or hippocampal-dependent memories) and in whom enhanced memory is desired or desirable. Exemplary subjects include humans, non-human mammals (such as, primates, canines, felines, or rodents), or avians.

In some embodiments, a subject has no known or detectable memory deficit (and may be referred to as a "normal subject"). In particular instances, such normal subjects may simply desire to improve their native memory. In other embodiments, a subject may be in a demographic group at some or even substantial risk for memory impairment; for example, aged subjects (e.g., older than 50 years of age, older than 60 years of age, older than 70 years of age, or even older than 80 years of age) and/or subjects having a genetic or other (e.g., environmental) predisposition to a memory-impairing disease, such as dementia, Alzheimer's disease, meningioma, depression, stroke/ischemia, or Parkinson's disease. Alternatively, subjects can be selected using more specific criteria, such as a probable or definitive diagnosis of memory-impairing disease based on, for example, clinical signs and symptoms and/or laboratory evidence of memory loss. For example, diseases involving loss of memory function may present clinically with increasing problems with short-term memory that interfere with daily functioning, such as forgetting what car keys are used for, difficulty recognizing friends and family, placing items in atypical places (for instance placing an iron in the refrigerator), forgetting how to do familiar activities like cooling, making repairs, or balancing a checkbook, throwing bills away before paying them, losing interest in friends or hobbies, or becoming more upset or angrier than usual. Exemplary memory-impairing diseases that a subject may have (or be thought to have) include, for example, dementia, Alzheimer's disease, meningioma, depression, stroke/ischemia, Parkinson's disease, learning disability, retardation, or age-associated memory impairment.

In some method embodiments, a subject does not have amyloidosis (also referred to as amyloid disorder) or a disease characterized by α-synuclein fibril formation (as either disorder is described is PCT Publication No. WO 2001/049281). Amyloid disorders are a group of diseases (including, e.g., Alzheimer's disease) characterized by the deposit of amyloids having the following characteristics: (i) showing an amorphous appearance at the light microscopic level, appearing eosinophilic using hematoxylin and eosin stains; (ii) staining with Congo red and demonstrating a red/green birefringence as viewed under polarized light (Puchtler et al., *Histochem. Cytochem.,* 10:355-64, 1962); (iii) containing a predominant beta-pleated sheet secondary structure; and (iv) consisting of non-branching fibrils of indefinite length and with a diameter of 7-10 nm. A prototypical disease characterized by α-synuclein fibril formation is Parkinson's disease. α-synuclein is a 140-amino acid protein (Ueda et al., *Proc. Natl. Acad. Sci. USA,* 90:11282-6, 1993), which forms filaments found in the Lewy bodies observed in Parkinson's disease (Lewy, In: *Handbuch der Neurologie,* ed. by Lewandowski, Berlin: Springer, pp. 920-933, 1912; Pollanen et al., *J. Neuropath. Exp. Neurol.,* 52:183-91, 1993).

Memory is the ability of a subject to store, retain, and subsequently recall information. The disclosed methods contemplate enhancing memory in general and/or improving one or more specific types of memory. In some method embodiments, memory can be sensory memory (lasting from milliseconds to seconds), short-term memory (lasting from seconds to minutes), or long-term memory (lasting days to years). In particular embodiments, long-term memory can be declarative (or explicit) memory, which involves consciously recalling specific items of information (such as, an answer to an exam question or what you had for breakfast), or procedural (or implicit) memory, which involves unconscious recollection of prior experience (such as, driving a car, remembering the rules of the road as well as the skills necessary to drive). In even more particular embodiments, declarative memory can be semantic memory, which concerns facts taken independent of context; and episodic memory, which concerns information specific to a particular context (such as a time and place). In still other embodiments, memory can be retrospective memory, which involves content from the past, or prospective memory, which involves memory for future intentions (eg., remembering to remember). Retrospective memory includes semantic memory and episodic/autobiographical memory (discussed above). Other method embodiments involve working memory, which refers to a short-term memory specific for certain mental tasks. Working memory is not typically considered synonymous with short-term memory because it is defined by purpose not by duration. Working memory is used, for instance, to store instructions and intermediate results when performing a series of mental calculations (additions and multiplications) to arrive at the final answer.

Memory enhancement can be determined by any known method, including subjective and/or objective methods, and/or qualitative and/or quantitative methods. Exemplary methods involve objective determination(s) of memory improvement in a subject. In examples where quantitative results are used to identify memory enhancement, such results, typically, are compared with some normative standard, including data from groups of non-memory-impaired subjects (e.g., normal subjects) or data from the same subject at some earlier point in time (e.g., prior to onset of memory loss or at a younger age). Norms may also be based on age, nutritional state, gender, or other factors, and comparison can be made between a subject's performance and that of other subjects in the selected normative group.

In some subjects, administration of a 5-desoxy flavone or 5-desoxy flavonol (e.g., a 5(H)-flavone, a 5(H)-flavonol, such as fisetin or any one or more of its derivatives as described in Examples 1-13) will cause a detectable improvement in the memory of the subject as compared to an untreated subject (or the treated subject prior to treatment). For example, a treated subject will improve its memory (or any specific type of memory) by at least about 10%, at least about 25%, at least about 50%, or at least about 75% as compared to a control (e.g., an untreated subject or the same subject prior to treatment).

Cognitive function tests useful for evaluating memory in a subject (such as, a human subject) include the Woodcock Johnson III Tests of Cognitive Abilities (WJ III), Working Memory Cluster, Delayed Recall Cluster, Long Term Retrieval Cluster, Short Term Memory Cluster, Re y A Verbal Learning Test (Rey, *L'examen Clinique En Psychologic*, Paris: Presses Universitaires de France, 1964), Test of Visual Perceptual Skills-Upper level (TVPS-UL-R), Hopkins Verbal Learning Test-Revised (Benedict el al. *Clin. Neuropsych.,* 12(1):43-55 1998), Continuous Visual Memory Test (CVMT) and as described in the Examples and Table 2.

TABLE 2

Exemplary cognitive function tests

| Test Name | Exemplary Purpose of Test |
| --- | --- |
| California Verbal Learning Test | This procedure examines several aspects of verbal learning, organization, and memory. Forms for adults and children. See, e.g., Delis et al., California Verbal Learning Test Manual, New York: The Psychological Corporation, 1987. |
| Cognistat (The Neurobehavioral Cognitive Status Examination) | This screening test examines language, memory, arithmetic, attention, judgment, and reasoning. It is typically used in screening individuals who cannot tolerate more complicated or lengthier neuropsychological tests. |
| Dementia Rating Scale | Provides measurement of attention, initiation, construction, conceptualization, and memory to assess cognitive status in older adults with cortical impairment. |
| Halstead-Reitan Neuropsychological Battery | A set of tests that examines language, attention, motor speed, abstract thinking, memory, and spatial reasoning is often used to produce an overall assessment of brain function. Some neuropsychologists use some or all of the original set of tests in this battery. |
| Memory Assessment Scales | This is a comprehensive battery of tests assessing short-term, verbal, and visual memory. |
| Rey Complex Figure Test | This drawing and visual memory test examines ability to construct a complex figure and remember it for later recall. It measures memory as well as visual-motor organization. |
| Rey 15-item Memory Test | This test is used to evaluate potential for malingering in memory. |
| Rey-Osterrieth Complex Figure Test | Analyzes aspects of visual-spatial ability and memory in all ages. |
| Rivermead Behavioural Memory Test | Evaluates impairments in everyday memory related to real life situations. |
| Test of Memory Malingering | This test is used to evaluate potential for malingering in memory. |

TABLE 2-continued

Exemplary cognitive function tests

| Test Name | Exemplary Purpose of Test |
| --- | --- |
| Test of Memory and Learning (TOMAL) | This test for children and adolescents measures numerous aspects of memory, assessing learning, attention, and recall. |
| Test of Memory Malingering | For ages 16-84, this visual recognition test helps discriminate malingered from true memory impairments. |
| Wechsler Adult Intelligence Scale-III | A set of 13 separate "subtests" produces measures of memory, knowledge, problem solving, calculation, abstract thinking, spatial orientation, planning, and speed of mental processing. In addition to summary measures of intelligence, performance on each subtest yields implications for different neurofunctional domains. The set of tests takes about an hour or more to administer. The WAIS-III is often the foundation for a comprehensive neuropsychological assessment. |
| Wechsler Intelligence Scale for Children-III | Comparable to the Wechsler Adult Intelligence Scale, this procedure contains subtests that measure similar domains in children. |
| Wechsler Memory Scale-III | A set of 18 separate "subtests" yields information about various kinds of memory and learning processes. Summary memory indices are provided in addition to the individual scores of the subtests. The whole set of tests takes about an hour to administer. The WMS-III provides a comprehensive assessment of memory. It is co-normed with the WAIS-III and is usually used in conjunction with it. |
| Word Memory Test | A validity procedure designed to detect response bias that might indicate exaggeration of impairment or symptom feigning. |

Routes of administration useful in the disclosed methods include but are not limited to oral and parenteral routes, such as intravenous (iv), intraperitoneal (ip), subcutaneous (sc), intramuscular (im), rectal, topical, ophthalmic, nasal, or transdermal. Formulations for these dosage forms are described elsewhere herein.

A "therapeutically effective amount" or "effective amount" is a quantity of a specified composition (e.g., 5-desoxy-flavone or 5-desoxy-flavonol or a hydrate or pharmaceutically acceptable salt of either thereof) sufficient to achieve a desired effect in a subject to whom the composition is being administered. For example, this may be an amount of a composition necessary to enhance memory and/or prevent, inhibit, reduce or relieve memory loss in a subject, preferably without causing a substantial cytotoxic effect on host cells. An effective amount of a 5-desoxy-flavone or S-desoxy-flavonol or a hydrate or pharmaceutically acceptable salt of either thereof will depend, at least, on the particular method of use, the subject being treated, the severity of the affliction and the manner of administration of the therapeutic composition. It is anticipated that memory-enhancing flavonoids described for use in the disclosed methods will be well tolerated in animal subjects (such as humans) because such compounds are naturally found in edibles consumed by such animals, Therapeutically effective doses of a described flavonoid (e.g., 5-desoxy flavone or 5-desoxy flavonol (such as, fisetin or its derivatives as described in any of Examples 1-13)) or pharmaceutical composition including the same can be determined by one of skill in the art. In some instances, an effective dose achieves a local (e.g., tissue) concentration that is at least as high as the $EC_{50}$ for neural protection or neural differentiation of the applicable compound disclosed in the examples herein; for example, from about 0.25 µM to about 200 µM, from about 0.5 µM to about 150 M, from about 0.75 µM to about 100 µM, from about 1 µM to about 75 µM, from about 1.5 µM to about 50 µM, from about 2.0 µM to about 40 µM, or from about 2.5 µM to about 20 µM (also, see Table 3 and/or 4).

In other methods, an exemplary dosage range is from about 0.1 to about 200 mg/kg body weight orally in single or divided doses (such as from about 5 mg/kg to about 200 mg/kg). In particular examples, a dosage range is from about 1.0 to about 100 mg/kg body weight orally in single or divided doses, including from about 1.0 to about 50 mg/kg body weight, from about 1.0 to about 25 mg/kg body weight, from about 1.0 to about 10 mg/kg body weight, or from about 10 to about 25 mg/kg body weight (assuming an average body weight of approximately 70 kg; values adjusted accordingly for persons weighing more or less than average).

For oral administration, one or more memory-enhancing flavonoids (e.g., 5-desoxy flavone or 5-desoxy flavonol (such as, fisetin or its derivatives as described in any of Examples 1-13)) are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g. from about 250 to about 500 mg) each 6 to 24 hours for at least 3 days. In another exemplary oral dosage regimen, a tablet containing from about 500 mg to about 1000 mg active ingredient is administered once per day on a continuing basis, for instance, for the remainder of a subject's life or until a desired improvement in memory has been achieved (e.g. as determined subjectively or by an objective measure).

The specific dose level and frequency of dosage for any particular subject may be varied and will depend upon a variety of factors, including the activity of a specific flavonoid, the metabolic stability and length of action of that compound, the age, body weight, general health, sex and diet of the subject, mode and time of administration, rate of excretion, drug combination, and severity of the condition of the host undergoing therapy.

The present disclosure also contemplates combinations of one or more disclosed memory-enhancing flavonoids (e.g., 5-desoxy flavone or 5-desoxy flavonol (such as, fisetin or its derivatives as described in any of Examples 1-13)) with each other and/or with one or more other agents or therapies useful to improve memory and/or treat or prevent memory-impairing disease. For example, one or more memory-enhancing flavonoids described for use in a disclosed method may be administered in combination with effective doses of other medicinal and/or pharmaceutical agents (such as, nutraceuticals, vitamins, antioxidants, prescription medications, trace minerals, and the like), or in combination other therapies, such as hypnosis, acupuncture, or other so-called alternative medicines. The term "administration in combination with" refers to both concurrent and sequential administration of active agents. In some examples, the one or more other agents or therapies include vinpocetine (Cavinton™), piracetam (Nootropil™), or antioxidants (such as, Vitamin C, Vitamin E, alpha-carotene, beta-carotene, Coenzyme Q, selenium, zinc, manganese, lycopene, lutein, zeaxanthin, astaxanthin, or as otherwise known in the art).

Flavonoids useful in a disclosed method (e.g., 5-desoxy flavone or 5-desoxy flavonol (such as, fisetin or its derivatives as described in any of Examples 1-13)) can be formulated in any manner useful for an intended application. Formulations for pharmaceutical compositions are well known in the art. For example, *Remington's Pharmaceutical Sciences*, by E. W. Martin, Mack Publishing Co., Easton, Pa., 15th Edition, 1975, describes exemplary formulations (and components thereof) suitable for pharmaceutical delivery of a composition of interest (such as, fisetin and/or other 5-desoxy flavonols and/or 5-desoxy flavones).

Compounds useful in the disclosed methods can be formulated for use in human or veterinary medicine. Particular formulations of a composition may depend, for example, on the mode of administration (eg., oral or parenteral) and/or a need to facilitate passage of the blood-brain barrier. In some embodiments, formulations include a pharmaceutically acceptable carrier in addition to at least one active ingredient, such as, fisetin and/or other 5-desoxy flavonols and/or 5-desoxy flavones. In other embodiments, other medicinal or pharmaceutical agents, for example, with similar, related or complementary effects on the condition or affliction being treated (such as memory loss), can also be included as active ingredients in a composition useful in a disclosed method.

Pharmaceutically acceptable carriers suitable for compositions useful in disclosed methods are conventional in the art. The nature of a pharmaceutical carrier will depend on the particular mode of administration being employed. For example, parenteral formulations usually involve injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The dosage form of a composition useful in a disclosed method will be determined by the mode of administration chosen; for example, injectable fluids and/or topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

EXAMPLES

The following examples are provided to illustrate certain particular features and/or embodiments. These examples should not be construed to limit the invention to the particular features or embodiments described.

Example 1

Fisetin and its Derivatives Induce Nerve Cell Differentiation

Fisetin is known to induce the differentiation of PC12 cells in an ERK-dependent manner (Sagara et al., *J. Neurochem.*, 90:1144-55, 2004). This Example demonstrates the structure-activity relationship between fisetin (3,7,3',4'-tetrahydroxyflavone) and its derivatives and nerve cell differentiation.

Four trihydroxyflavones (THF) and three dihydroxyflavones (DHF) which lack one or two, respectively, of the hydroxyl groups found in fisetin were tested for their ability to induce the differentiation of PC12 cells. Differentiation was assessed by scoring neurite outgrowth (Sagara et al., *J. Neurochem.*, 90:1144-1155, 2004).

As shown in Table 3, all of these fisetin derivatives exhibited some ability to induce differentiation although there was variation in both their potency and efficacy. The compound, 3,3',4'-THF, was the most effective of those tested and induced the differentiation of >80% of the PC12 cells at a concentration of 5 μM.

TABLE 3

Induction of PC12 Cell Differentiation

| Flavonoid | $EC_{50}$ (μM) | Maximal Efficacy |
|---|---|---|
| 3,3'-DHF | 10 | 40-50% |
| 3,4'-DHF | 20 | 50-60% |
| 3',4'-DHF | 10 | 40-50% |
| 3,3',4'-THF | 2.5 | 80-90% |
| 3,7,3'-THF | 15 | 40-50% |
| 3,7,4'-THF | 10 | 70-80% |
| 7,3',4'-THF | 10 | 50-60% |
| 3,7,3',4'-THF (fisetin) | 5 | 70-80% |

Half maximal effective concentration ($EC_{50}$) and maximal efficacy for differentiation were determined by exposing PC12 cells to different concentration of each flavonoid and assessing differentiation as described in Example 4.

This Example shows that two fisetin derivatives, 3,3',4'-TH-F and 3,7,4'-THF, like fisetin, promote the differentiation of 75-80% of the cells. Although 3,7,4'-THF is somewhat less potent than fisetin with an $EC_{50}$ of 10 μM, 3,3',4'-THF is more potent with an $EC_{50}$ of 2.5 μM. 3,4'-DHF is slightly less efficacious and potent than fisetin but still better than all of the other derivatives tested.

Taken together these data indicate several requirements for the differentiation promoting activity of flavonoids. First, three hydroxyl groups appears to be optimal for the induction of differentiation. Both the removal or addition of hydroxyl groups to 3,3',4'-THF reduces its differentiating promoting activity. Fisetin, with one additional hydroxyl (at position 7), is less effective than 3,3',4'-THF but much better than quercetin (with two additional hydroxyls at positions 7 and 5) while myricetin (with three additional hydroxyls at positions 7, 5 and 5'), is completely ineffective. Second, of the three hydroxyl groups present in 3,3',4'-THF, the 4' hydroxyl appears to be important for good differentiation-promoting activity since derivatives without this group are less effective.

Example 2

Fisetin Derivatives Induced ERK Activation with a Delayed Time Course

Fisetin activates ERK and fisetin-induced differentiation is dependent upon the activation of this kinase (Sagara et al., *J. Neurochem.*, 90:1144-1155, 2004). This Example demonstrates that fisetin derivatives also activate ERK.

PC12 cells were treated with the optimal concentrations for differentiation of the different derivatives for 10 minutes to 6 hours; then the cells were scraped into sample buffer and analyzed by SDS-PAGE and immunoblotting with an antibody specific for phosphorylated ERKs (anti-phospho ERK) and an antibody that detects phosphorylated and unphosphorylated ERKs (anti-ERK), All of the fisetin derivatives induced ERK activation with a delayed time course similar to that of fisetin For example, FIG. 1A shows a time course of ERK activation in PC12 cells treated with 5 µM 3,3',4'-THF for 10 minutes to 6 hours. Similar results were obtained in three independent experiments.

ERK activation by the different flavonoids was blocked by pretreatment with PD98059, an inhibitor of MEK, the kinase which phosphorylates ERK. PC12 cells in N2 medium were untreated (control) or treated with 10 µM fisetin, 25 µM 3,3'-DHF, 25 µM 3,4'-DHF, 25 µM 3',4'-DHF, 5 µM 3,3',4'-THF, 25 µM 3,7,3'-THF, 25 µM 3,7,4'-THF or 10 µM 7,3',4'-THF for 4 hours in the absence or presence of 50 µM PD98059 (30 minutes pretreatment). The cells then were scraped into sample buffer and analyzed by SDS-PAGE and immunoblotting with an antibody specific for phosphorylated ERKs (anti-phospho ERK) and an antibody that detects phosphorylated and unphosphorylated ERKs (anti-ERK). FIG. 1B shows that PD98059 blocked ERK activation induced by fisetin derivatives. Similar results were obtained in two independent experiments.

Figure 2:
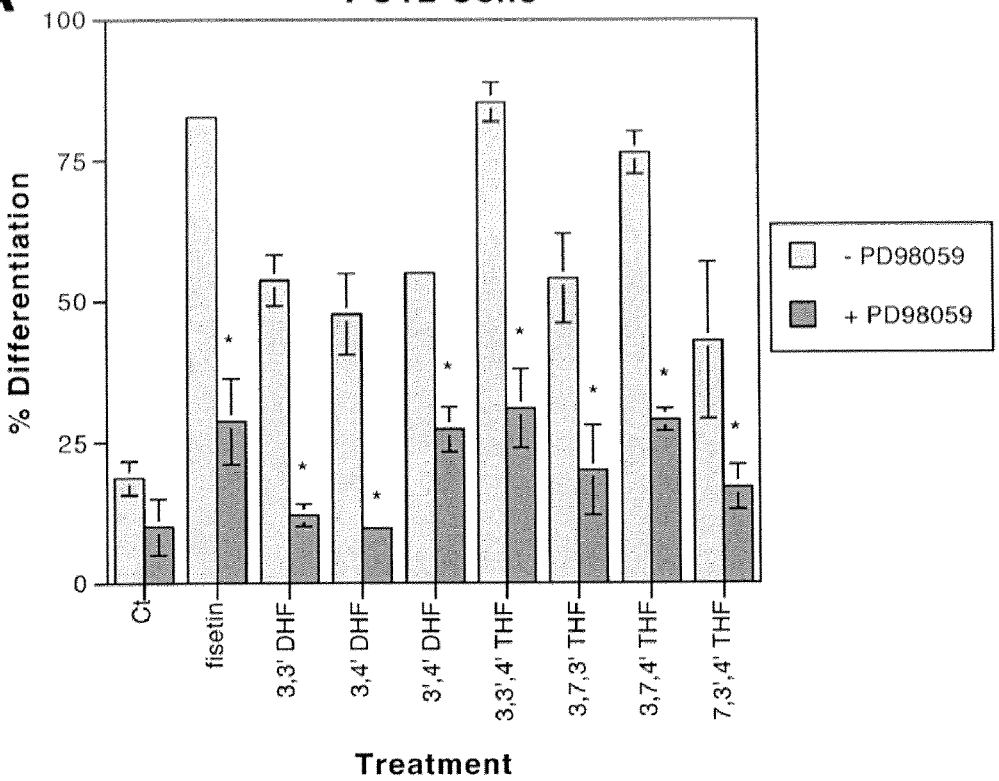
FIG. 2A shows the percentage of differentiated PC12 cells in the presence of fisetin or the indicated fisetin derivatives (light bars) or in the presence fisetin or the indicated fisetin derivatives and the MEK inhibitor, PD98059 (dark bars). The MEK inhibitor blocks fisetin- or fisetin-derivative-induced PC12 cell differentiation. The results presented are the average±S.D. of 2-3 independent experiments. * indicates a significant difference between the cells treated with PD98059 and those treated without PD98059.
FIG. 2B shows the percentage HT12 cell survival in the presence of fisetin or the indicated fisetin derivatives (light bars) or in the presence fisetin or the indicated fisetin derivatives and the MEK inhibitor PD98059 (dark bars). The MEK inhibitor does not block fisetin- or fisetin-derivative-induced HT22 cell protection from oxidative glutamate toxicity. The results presented are the average±S.D. of two independent experiments.
Figure 2:
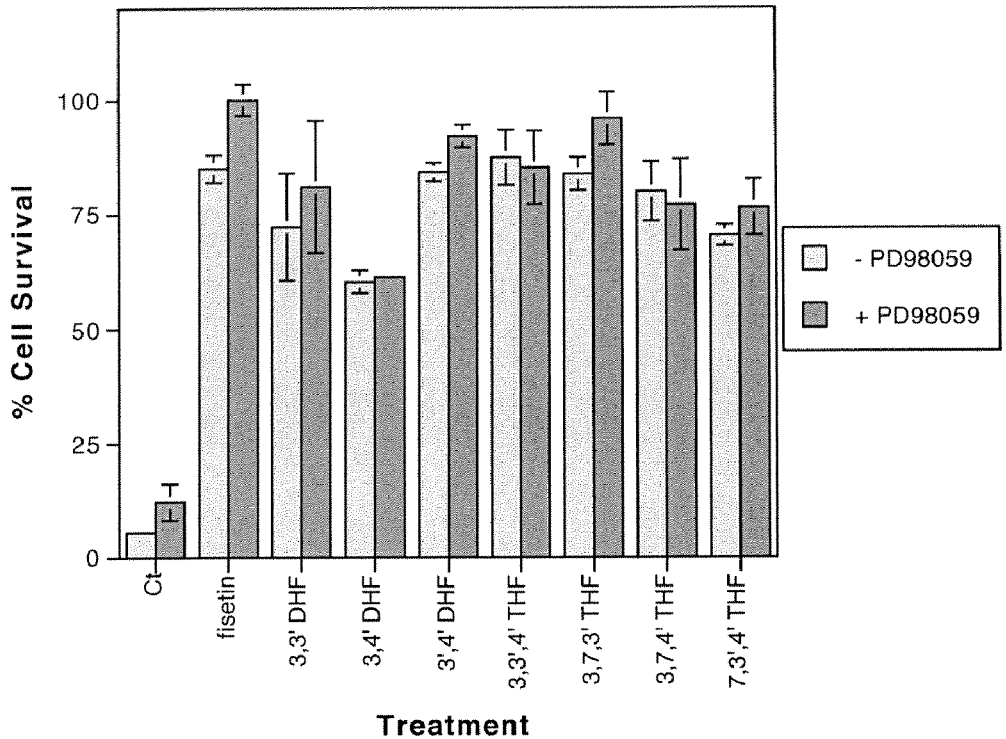

To determine if the differentiation seen following treatment with the fisetin derivatives was dependent upon ERK activation, PC12 cells in N2 medium were untreated (Ct) or treated with 10 µM fisetin, 10 µM 3,3'-DHF, 25 µM 3,4'-DHF, 10 µM 3',4'-DHF, 5 µM 3,3',4'-THF, 25 µM 3,7,3'-THF, 25 µM 3,7,4'-THF or 10 µM 7,3',4'-THF in the absence or presence of 50 µM PD98059 (30 minutes pretreatment). Twenty-four (24) hours later, the cells were scored for the presence of neurites. For each treatment, 100 cells in each of three separate fields were counted. Cells were scored positive if one or more neurites>1 cell body diameter in length was observed. As shown in FIG. 2A, inhibition of ERK activation reduced the differentiation induced by all of the fisetin derivatives.

Similar to fisetin, all of the fisetin derivatives induce ERK activation (FIG. 1) and this effect is correlated with the promotion of differentiation since the MEK inhibitor PD98059 reduces the differentiation induced by all of the derivatives. All of the fisetin derivatives tested also show the delayed time course of ERK activation that is observed with fisetin further indicating that they are all using a similar pathway for activation. However, since the efficacy of ERK activation is not in precise agreement with the ability of the different derivatives to promote differentiation and PD98059 does not completely block differentiation, in all cases, other signaling pathways may contribute to the differentiation-inducing activity of some of the derivatives Example 3

Fisetin Derivativfes Protected Nerve Cells from Oxidative Stress-Induced Death

Fisetin is effective at protecting nerve cells from oxidative stress-induced death (Ishige et al., *Free Radic. Biol. Med.*, 30:433-446, 2001). This Example illustrates the structure-activity relationship between fisetin derivatives and neuroprotection in a model of oxidative glutamate toxicity using mouse HT22 cells. This pathway of programmed cell death is initiated by the addition of glutamate to the extracellular medium. Glutamate inhibits the uptake of cystine which is required for glutathione (GSH) biosynthesis, resulting in the depletion of GSH in neurons (for review see Tan et al., *Curr. Top. Med. Chem.*, 1:497-506, 2001). Subsequently, this decrease in cellular GSH results in the production of reactive oxygen species (ROS) by mitochondria. The ROS accumulation then causes $Ca^{+2}$ influx from the extracellular medium which leads to cell death.

Fisetin previously was shown to both act as an antioxidant and to maintain the intracellular levels of GSH (Ishige et al., *Free Radic, Biol. Med.*, 30:433-446, 2001). All of the fisetin derivatives were effective at preventing cell death in this model of neuronal oxidative stress (Table 4).

TABLE 4

Protection from Oxidative-Stress Induced Death

| Flavonoid | $EC_{50}$ (µM) | Maximal Efficacy | TEAC |
|---|---|---|---|
| 3,3'-DHF | 12 | >80% | 1.01 ± 0.01 |
| 3,4'-DHF | 10 | >70% | 0.62 ± 0.06 |
| 3',4'-DHF | 0.9 | >90% | 1.24 ± 0.08 |
| 3,3',4'-THF | 0.75 | >90% | 2.07 ± 0.06 |
| 3,7,3'-THF | 17 | >90% | 1.55 ± 0.34 |
| 3,7,4'-THF | 12.5 | >90% | 1.01 ± 0.10 |
| 7,3',4'-THF | 5 | >80% | 0.89 ± 0.04 |
| 3,7,3',4'-THF (fisetin) | 5 | >90% | 3.11 ± 0.20 |

Half maximal effective concentrations ($EC_{50}$) and maximal efficacy for protection were determined by exposing HT22 cells to different concentrations of each flavonoid in the presence of 5 mM glutamate.
Cell viability was determined after 24 hours by the MTT assay.
TEAC values were determined using the ABTS decolorization assay with Trolox as a reference as described in Example 4.

Similar to the results with the differentiation assay, 3,3',4-THF was found to be more effective than fisetin with an $EC_{50}$) of 1 µM and >85% protection seen at 2.5 µM. However, unlike the differentiation assay. 3',4'-DHF also was more effective than fisetin.

In contrast to the differentiation assay the protection against oxidative stress afforded by fisetin and its derivatives did not appear to be dependent upon ERK activation. HT22 cells were untreated (Ct) or treated with 10 µM fisetin, 25 µM 3,3'-DHF, 25 µM 3,4'-DHF, 2.5 µM 3',4'-DHF, 2.5 µM 3,3', 4'-THF 25 µM 3,7,3'-THF, 25 µM 3,7,4'-THF or 10 µM 7,3', 4'-THF in the presence of 5 mM glutamate±50 µM PD98059. Twenty four (24) hours later cell survival was measured by the MTT assay. As shown in FIG. 2B, the MEK inhibitor, PD98059, had no significant effect on the ability of fisetin or its derivatives to prevent cell death.

A. No Correlation between Antioxidant Activity and Protection from Oxidative Stress-Induced Death To determine if the protection seen with the different fisetin derivatives correlated with their antioxidant properties, their Trolox Equivalent Activity Concentration (TEAC) values were determined. In this procedure, a compound is compared to Trolox, a water-soluble vitamin E analog, for its ability to reduce the radical cation of ABTS in aqueous solution. As reported previously, fisetin has a TEAC value of ~3 (Table II). None of the derivatives had TEAC values in this range despite, in some cases, showing better protection against oxidative stress-induced death. Thus, there was no correlation with antioxidant activity as defined by TEAC value and protection in this system.

B. Fisetin Derivatives, Except 3,3',4'-THF, Protect Nerve Cells From Toxic Oxidative Insults by GSH-Independent Mechanism(s)

In addition to being a relatively good antioxidant, part of the protection against oxidative stress provided by fisetin is due to its ability to maintain GSH levels (Ishige et al., *Free Radic. Biol. Med.*, 30:433-446, 2001). To determine if the ability to maintain GSH levels also plays a role in the protection mediated by the fisetin derivatives, the effect of buthionine sulfoximine (BSO) on protection was examined. BSO inhibits glutamate cysteine ligase, the rate limiting enzyme in GSH biosynthesis, leading to a time-dependent decrease in GSH levels.

Figure 3:
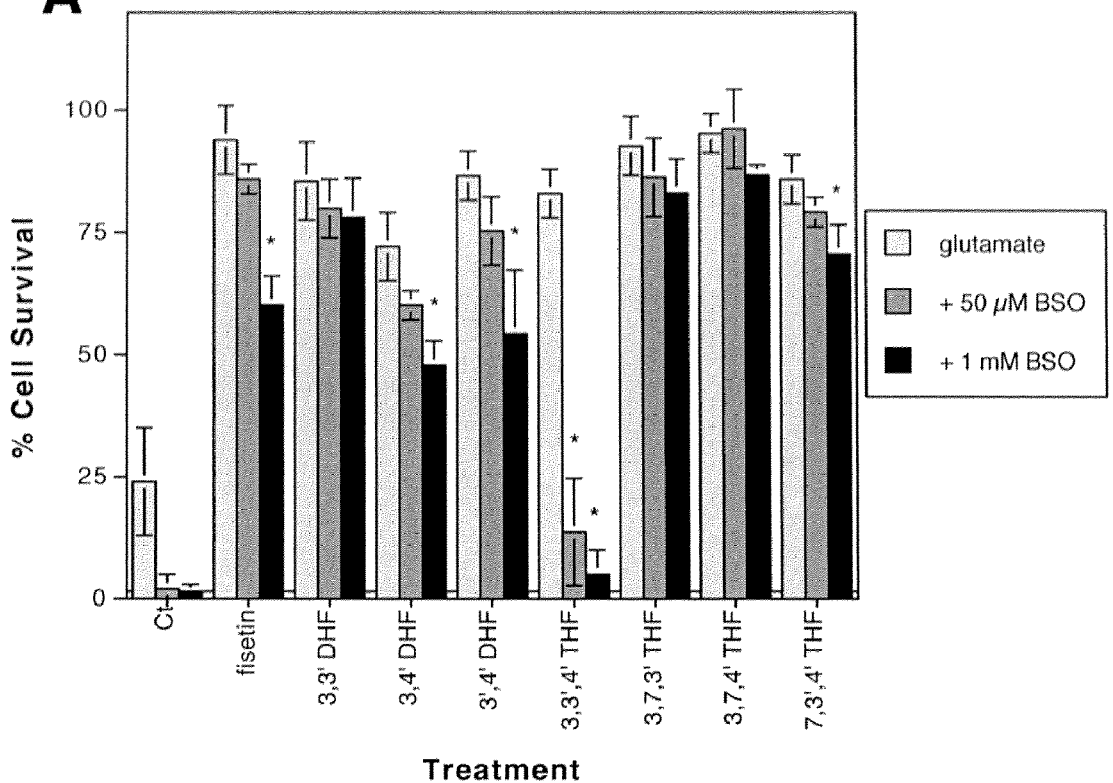
FIG. 3A shows the percentage HT22 cell survival in the presence of fisetin or the indicated fisetin derivative and glutamate alone (light bars), 50 µM buthionine sulfoximine (BSO) (medium bars), or 1 mM BSO (dark bars). Protection by fisetin or its derivatives is differentially affected by BSO. The results presented are the average±S.D. of five independent experiments. * indicates a significant difference between the cells treated with BSO and those treated without BSO.
FIG. 3B shows the effects of fisetin or the indicated fisetin derivative on HT22 cellular GSH levels in the absence (light bars) or presence of glutamate (dark bars). The results are the means±SD of duplicate determinations from 3-5 independent experiments. * indicates a significant difference between the control (Ct) and the sample treated with a fisetin derivative.
Figure 3:
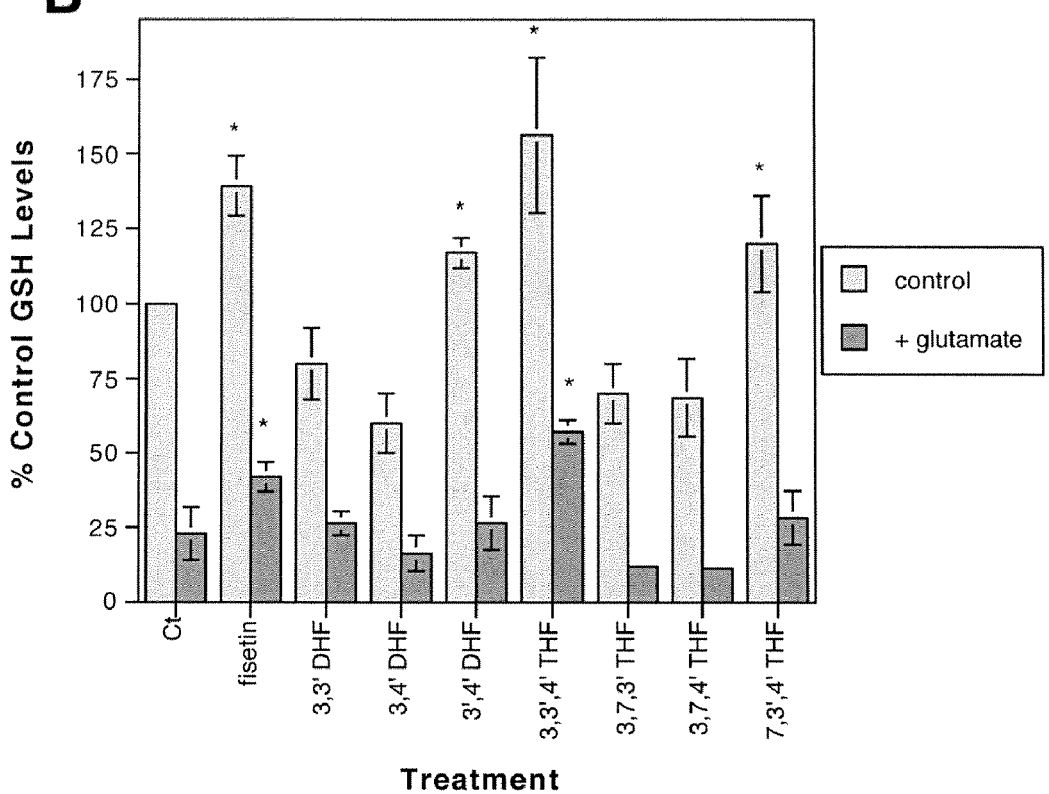

HT22 cells were untreated (Ct) or treated with 10 μM fisetin, 25 μM 3,3'-DHF, 25 μM 3,4'-DHF, 2.5 μM 3',4'-DHF, 2.5 μM 3,3',4'-THF, 25 μM 3,7,3-THF, 25 μM 3,7,4'-THF or 10 μM 7,3',4'-THF in the presence of 5 mM glutamate±50 μM BSO or 1 mM BSO, Twenty four (24) hours later cell survival was measured by the MTT assay, As shown in FIG. 3A, low levels of BSO significantly reduced protection by 3,3',4'-THF. Higher levels reduced protection by fisetin, 3,4'-DHF, 3',4'-DHF and 7,3',4-THF. Protection by all of the other flavonoids was unaffected by BSO.

The effects of fisetin derivatives on cellular GSH levels was then determined. HT22 cells were untreated (Ct) or treated with 10 μM fisetin, 25 μM 3,3'-DHF, 25 μM 3,4'-DHF, 2.5 μM 3',4'-DHF, 2.5 μM 3,3',4'-THF, 25 μM 3,7,3'-THF, 25 μM 3,7,4'-THF or 10 μM 7,3',4'-THF alone or in the presence of 5 mM glutamate. After 8 hours cellular levels of total GSH were determined as described in Example 4. The GSH level of the control sample (31.5±10 nmoles/mg protein) was taken as 100%.

Among the fisetin derivatives, only 3,3',4'-THF was able to maintain GSH levels in the presence of oxidative stress (see FIG. 3B) while both 3',4'-DHF and 7,3',4'-THF raised the basal levels of GSH but could not maintain GSH levels in the presence of oxidative stress. These results suggest that all of the fisetin derivatives except 3,3',4'-THF protect nerve cells from toxic oxidative insults by GSH-independent mechanisms whereas protection by 3,3',4'-THF is dependent on its ability to enhance GSH levels in cells.

C. Fisetin and Some of Its Derivatives Increase Nrf2 Expression and Induce HO-1 Synthesis Mostly by an ERK-Independent Pathway Cells possess a number of different endogenous antioxidant defense mechanisms. Induction of phase II detoxification proteins can provide long-term protection of cells against oxidative stress. Several studies have shown that fisetin as well as other flavonoids can induce the activity and expression of phase II detoxification proteins (Valerio et al., *Toxicol. Lett.*, 119:49-57, 2001; Hou et al., *Int. J. Oncol.*, 18:1175-1179, 2001; Myhrstad et al., *Free Rad. Biol. Med.*, 32:386-393, 2002). The phase II detoxification proteins include enzymes associated with glutathione biosynthesis and metabolism and redox sensitive proteins such as heme oxygenase-1 (HO-1) (Hayes and McLellan, *Free Rad. Res.*, 31:273-300, 1999). The transcriptional activation of these and other genes encoding phase II detoxification proteins is mediated by a cis-acting enhancer termed the antioxidant response element (ARE). Transcriptional activation of the ARE is dependent upon the transcription factor NF-E2-related factor 2 (Nrf2), a member of the Cap'n'Collar family of bZIP proteins (Nguyen et al., *Ann. Rev. Pharmacol. Toxicol.*, 43:233-260, 2003).

Since the ability to activate the ARE could be important for some of the beneficial effects of flavonoids such as fisetin, it was determined which, if any, of the fisetin derivatives could activate the ARE and induce the synthesis of downstream proteins such as HO-1. HT22 cells were untreated (control) or treated with 10 μM fisetin, 25 μM 3,3'DHF, 25 μM 3,4'-DHF, 10 μM 3',4'-DHF, 10 μM 3,3',4'-THF, 25 μM 3,7,3'-THF, 25 μM 3,7,4'-THF or 10 μM 7,3',4'-THF for 4 hours. Nuclei were prepared and equal amounts of protein were analyzed by SDS-PAGE and immunoblotting with anti-Nrf-2 antibodies.

Figure 4:
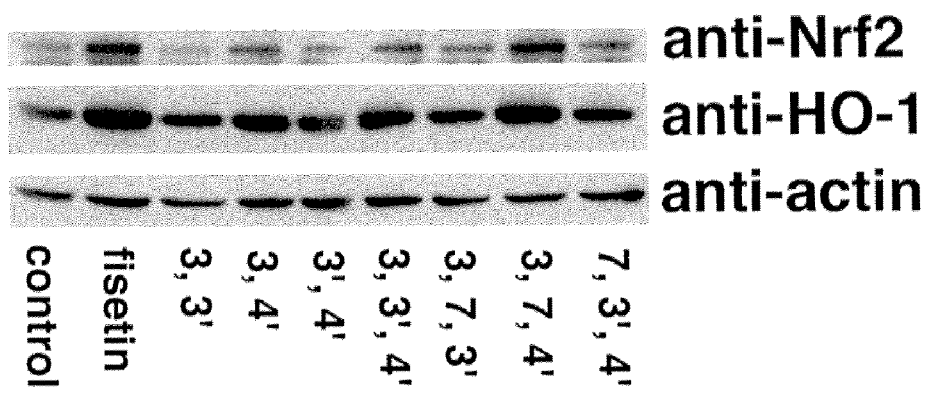
FIG. 4 shows a series of Western blots of cell extracts of HT22 cells untreated (control) or treated with fisetin or the indicated fisetin derivative and, where indicated in FIG. 4B, the MEK inhibitor, PD98059. The cell extracts were probed with the indicated antibodies (anti-Nrf2, anti-HO-1, or anti-actin).
Figure 4:
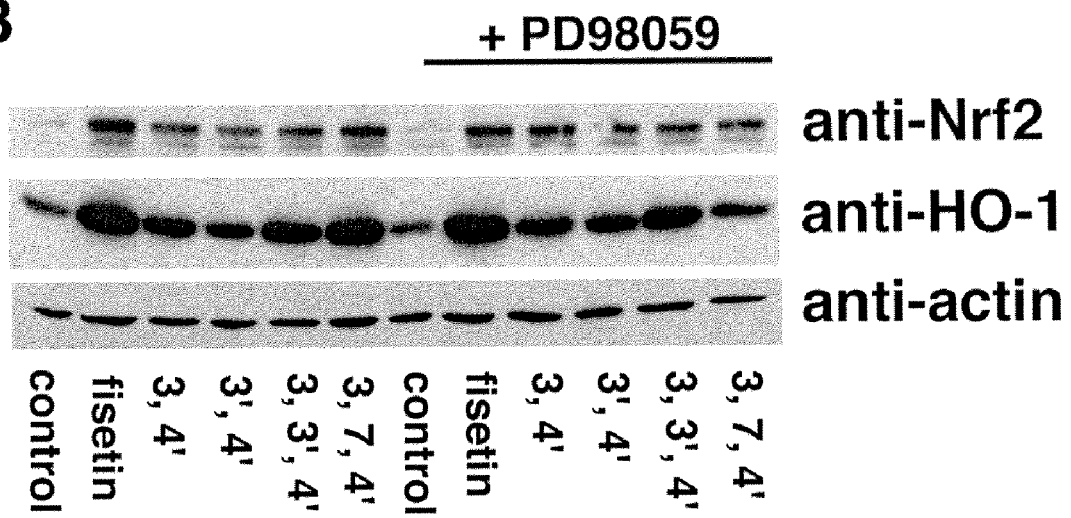

In contrast to the other assays, fisetin was the best of the group at increasing the levels of Nrf2 and inducing HO-1 synthesis (see FIG. 4A). Several of the fisetin derivatives were fairly effective, including 3,4'-DHF, 3,3',4'-THF and 3,7,4'-THF, and 3',4'-DHF was weakly active while the rest of the derivatives were inactive in this assay.

ERK activation is implicated in the induction of Nrf2 by certain stimuli in some cell types. To determine if ERK activation plays a role in the induction of Nrf2 and HO-1 by fisetin and its derivatives, cells were pretreated with PD98059 prior to the addition of the flavonoids to the cells. HT22 cells then were untreated (control) or treated for 24 hours with 10 μM fisetin, 25 μM 3,3'-DHF, 25 μM 3,4'-DHF, 10 μM 3',4'-DHF, 10 μM 3,3',4'-THF, 25 μM 3,7,3'-THF, 25 μM 3,7,4'-THF or 10 μM 7,3',4'-THF. Cell lysates were prepared and equal amounts of cellular protein were analyzed by SDS-PAGE and immunoblotting with anti-HO-1 antibodies. Immunoblotting with anti-actin was used as a loading control. As shown in FIG. 4B, inhibition of ERK activation reduced Nr12 and HO-1 induction by 3,7,4'-THF but had no effect on the induction by fisetin or any of the other active derivatives.

Earlier studies demonstrated that fisetin could protect nerve cells from oxidative stress-induced death (Ishige et al., *Free Radic. Biol. Med.*, 30:433-446, 2001). Unlike with the differentiation assay (see Example 1), a number of the fisetin derivatives were found to be equal to or more effective than fisetin in the protection assay. These include 3',4'-DHF, 3,3', 4'-THF and 7,3',4'-THF. However, unlike differentiation, protection from oxidative stress was not dependent upon ERK activation. Structure-activity analysis indicated that the 3',4'-catechol group is useful for maximal protection. However, the catechol group is not essential for protection since all of the other fisetin derivatives were reasonably effective at preventing oxidative stress-induced death The mechanisms underlying protection against oxidative stress-induced death appeared to differ among the fisetin derivatives. Only protection by 3,3',4'-THF was strongly dependent upon its ability to maintain GSH levels. Interestingly, antioxidant activity, as determined by measuring TEAC values, did not appear to play a major role in the protection by any of the fisetin derivatives. These results are consistent with prior reports (Ishige et al., *Free Radic. Biol. Med*, 30:433-446, 2001) that showed similar levels of potency and efficacy with respect to protection from oxidative stress-induced death can be achieved by different means, even among closely related molecules.

In contrast to the results for protection the ability to activate the ARE shows a reasonable correlation with the ability to induce differentiation (see Example 1). This suggests that the same pathways could be involved in the two actions of the flavonoids. However, except for 3,7,4'-THF, pretreatment with the MEK inhibitor PD98059 had little effect on Nrf2 induction or enhancement of HO-1 synthesis as compared with the effect on differentiation. This result may (but need not) mean that closely related molecules can utilize distinct signaling pathways in order to achieve the same outcome.

Example 4

Representative Materials and Methods

This Example provides representative materials and methods useful to obtain the results described in Examples 1-3.

A. Chemicals

Fisetin was from Sigma/Aldrich (St. Louis, Mo.). Other flavonoids were from Indofine Chemical Co. (Hillsborough, N.J.). PD98059 was from Promega (Madison, Wis.). All other chemicals were from Sigma.

B. Cell Culture

Fetal calf serum (FCS), dialyzed FCS (DFCS) and horse serum were from Hyclone (Logan, Utah). Dulbecco's Modified Eagle's Medium (DMEM) was purchased from Gibco (Carlsbad, Calif.). HT-22 cells (Davis and Maher, *Brain Res.*, 652:169-173, 1994; Maher and Davis, *J. Neurosci.*, 16:6394-6401, 1996) were grown in DMEM supplemented with 10% FBS and antibiotics PC12 cells (Greene and Tischler, *Proc. Natl. Acad. Sci. USA* 73:2424-2428. 1976) were maintained in Dulbecco's modified Eagle's medium supplemented with 10% horse serum (Hyclone), 5% FCS and antibiotics. To examine the effects of flavonioids and other agents on the PC12 cells, the culture medium was removed and replaced by the chemically defined N2 medium (Gibco) 18 hours prior to the start of the experiment.

C. Differentiation Assay

PC12 cells in N2 medium were treated with flavonoids for 24 hours at which time the cells were scored for the presence of neurites. PC12 cells produce neurites much more rapidly when treated in N2 medium than when treated in regular growth medium (Kimura et al., *J. Cell Biol.*, 116:777-83, 1992). For each treatment, 100 cells in each of three separate fields were counted. Cells were scored positive if one or more neurites>1 cell body diameter in length were observed.

D. Cytotoxicity Assay

Cell viability was determined by a modified version of the 3-(4,5-dimethylthiazol-2-yl)-2,5-diphenyl tetrazolium bromide (MTT) assay based on the standard procedure (Hansen et al., *J. Immunol. Meth.*, 119:203-10, 1989). Briefly, cells were seeded onto 96-well microtiter plates at a density of $5 \times 10^3$ cells per well. The next day, the medium was replaced with DMEM supplemented with 7.5% DFCS and the cells were treated with the different flavonoids alone or in the presence of 5 mM glutamate. Twenty four hours later, the medium in each well was aspirated and replaced with fresh medium containing 2.5 µg/ml MTT. After 4 hours of incubation at 37° C., cells were solubilized with 100 µl of a solution containing 50% dimethylformamide and 20% SDS (pH 4.7). The absorbance at 570 nm was measured on the following day with a microplate reader (Molecular Devices). Results obtained from the MTT assay correlated directly with the extent of cell death as confirmed visually. Controls employing wells without cells were used to determine the effects of the agents upon the assay chemistry.

E. SDS-PAGE and Immunoblotting

PC12 cells in N2 medium were treated with the flavonoids as described in the text and, after the indicated time periods, the cells were solubilized in SDS sample buffer containing 0.1 mM $Na_3VO_4$ and 1 mM phenylmethylsulfonyl fluoride (PMSF), boiled for 5 minutes and either analyzed immediately or stored frozen at −70° C. Proteins were separated on 10% SDS polyacrylamide gels and transferred to nitrocellulose. Equal loading and transfer of the samples was confirmed by staining the nitrocellulose with Ponceau-S. Transfers were blocked for 2 hours at room temperature with 5% nonfat milk in TBS/0.1% Tween 20 and then incubated overnight at 4° C. in the primary antibody diluted in 5% BSA in TBS/0.05% Tween 20. The primary antibodies used were: phospho-p44/42 MAP kinase antibody (#9101, 1/1000) from Cell Signaling (Beverly, Mass.) and pan ERK antibody (#E17120, 1/10000) from Transduction Laboratories (San Diego, Calif.). The transfers were rinsed with TBS/0.05% Tween 20 and incubated for 1 hour at room temperature in horseradish peroxidase-goat anti-rabbit or goat anti-mouse (Biorad, Hercules, Calif.) diluted 1/5000 in 5% nonfat milk in TBS/0.1% Tween 20. The immunoblots were developed with the Super Signal reagent (Pierce, Rockford, Ill.).

For immunoblotting of HO-1, untreated and flavonoid-treated HT22 cells from the same density cultures as used for the cell death assays were washed twice in cold phosphate-buffered saline (PBS) then scraped into lysis buffer containing 50 mM HEPES, pH 7.4, 150 mM NaCl, 50 mM NaF, 1.5 mM $MgC_2$, 1 mM EGTA, 10% glycerol, 1% Triton X-100, 10 mM sodium pyrophosphate, 1 mM $Na_3VO_4$, 1 mM phenylmethylsulfonyl fluoride (PMSF), 15 µg/ml aprotinin, 1 µg/ml pepstatin, and 5 µg/ml leupeptin. Lysates were incubated at 4° C. for 30 minutes, and then cleared by centrifugation at 14,000 rpm for 10 minutes. For immunoblotting of Nrl2, nuclear extracts were prepared as described (Schreiber et al., *Nuc. Acids Res.*, 17:6419, 1989) from untreated and flavonoid-treated cells. For each flavonoid, the concentration which was most effective at preventing cell death was used. Protein concentrations were determined using the BCA protein assay (Pierce). Equal amounts of protein were solubilized in 2.5×SDS sample buffer, separated on 10% SDS polyacrylamide gels and transferred to nitrocellulose. The primary antibodies used were: anti-Nrf2 (#SC13032; 1/1000) from Santa Cruz Biotechnology (Santa Cruz, Calif.) and anti-HO-1 (#SPA-896; 1/5000) from Stressgen (Victoria, BC Canada).

F. Total Intracellular GSH/GSSG

Total intracellular GSH/GSSG was determined using whole cell lysates from untreated, glutamate treated, flavonoid treated and glutamate plus flavonoid treated cells as described (Maher and Hanneken, Invest. *Opthalmol. Vis. Sci.*, 46:749-57, 2005, herein incorporated by reference as to the method) and normalized to total cellular protein. For each flavonoid, the concentration which was most effective at preventing cell death was used, G. Determination of the Trolox Equivalent Activity Concentration (TEAC)

TEAC values for the flavonoids were determined according to (Re et al. *Free Rad. Biol. Med.*, 26:1231-7, 1999) but modified for a plate reader. Briefly, 250 µl of 2,2'-azinobis(3-ethylbenzothiazoline 6-sulfonate)(ABTS) treated overnight with potassium persulfate and diluted to an OD of ~0.7 at 734 nm was added to 2.5 µl of a flavonoid solution in ethanol. The change in absorbance due to the reduction of the ABTS radical cation was measured at 734 nm for 4 minutes. To calculate the TEAC, the gradient of the plot of the percentage inhibition of absorbance vs. concentration for the flavonoid in question is divided by the gradient of the plot for Trolox.

H. Statistical Analysis

Experiments presented were repeated at least three times. The data are presented as the mean SD. An unpaired Student's t-test was used to compare the data obtained.

Example 5

Fisetin Promotes ERK and CREB Activation in Primary Cortical Neuron Cultures

Fisetin is known to induce the differentiation of PC12 cells in an ERK-dependent manner (Sagara et al., *J. Neurochem.*, 90:1144-1155, 2004 and Example 1). ERK activation is believed to be involved not only in differentiation but also in the promotion of nerve cell survival and the induction of synaptic function (Sweatt, *Curr. Opin. Neurobiol.*, 14:311-317, 2004). One of the key signaling molecules activated downstream of ERK is the transcription factor CREB which is believed to be involved in learning and memory as well as nerve cell survival (Carlezon et al., *Trends Neurosci.*, 28:436-445, 2005). This Example illustrates that fisetin promotes ERK activation and enhances CREB activation in primary cultures of cortical neurons.

Figure 5:
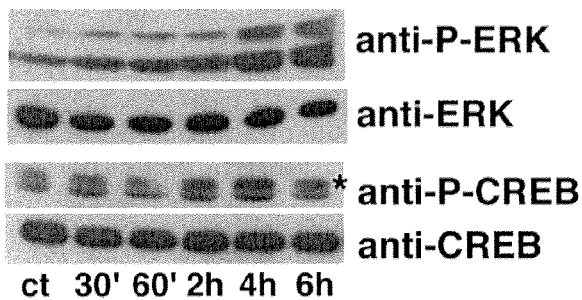
FIG. 5 shows Western blots (panels A and C) of primary cortical neuron extracts untreated (ct) or treated as described in Example 5, which blots were probed with the indicated antibodies. Bar graphs quantifying the results of Western blots are shown in panels B and D. The average phosphoprotein signal from the blots was quantified by densitometry and normalized to total protein was plotted±S.D.
Figure 5:
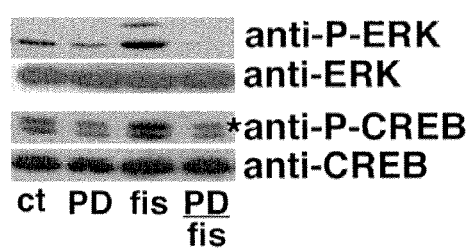
Figure 5:
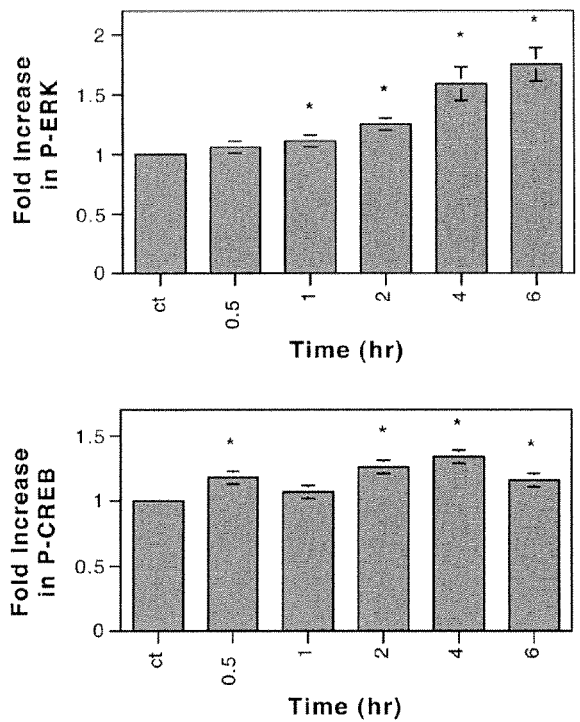
Figure 5:
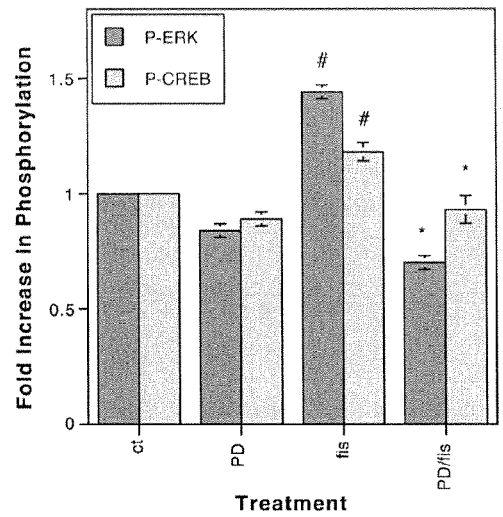
Figure 10:
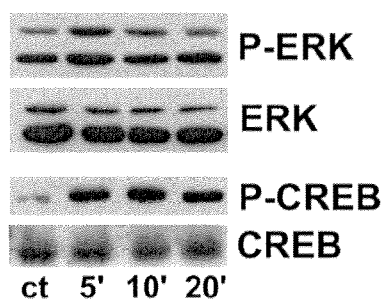
FIG. 10 shows that fisetin activates ERK1 (p44), ERK2 (p42) and CREB in rat hippocampal slices. Western blots panels A and B) of hippocampal slices treated with (A) 1 µM fisetin or (B) pretreated for 30 minutes with either 50 µM PD98059 (PD) or 10 µM U0126 (U) before the addition of 1 µM fisetin for 5 minutes, which blots were probed with the indicated antibodies. Bar graphs quantifying the results of Western blots are shown in panels C and D. The average phosphoprotein signal from the blots, quantified by densitometry and normalized to total protein was plotted±S.D.
Figure 10:
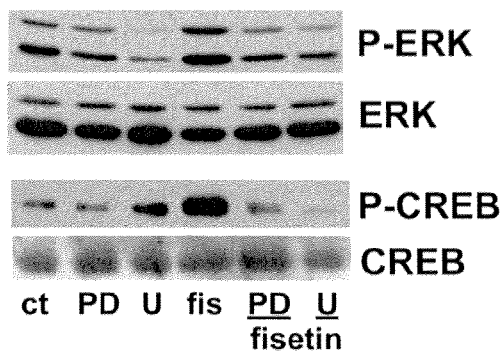
Figure 10:
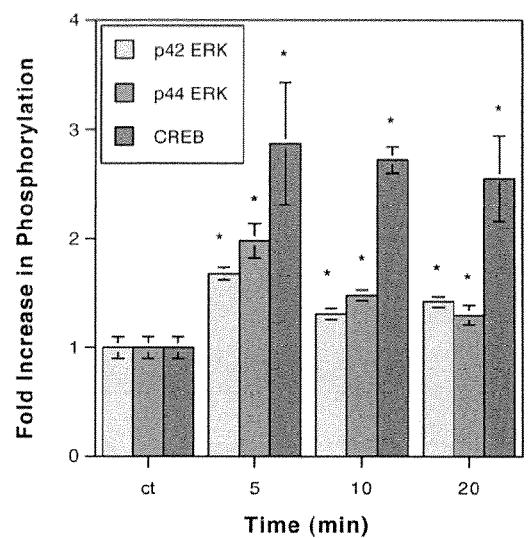
Figure 10:
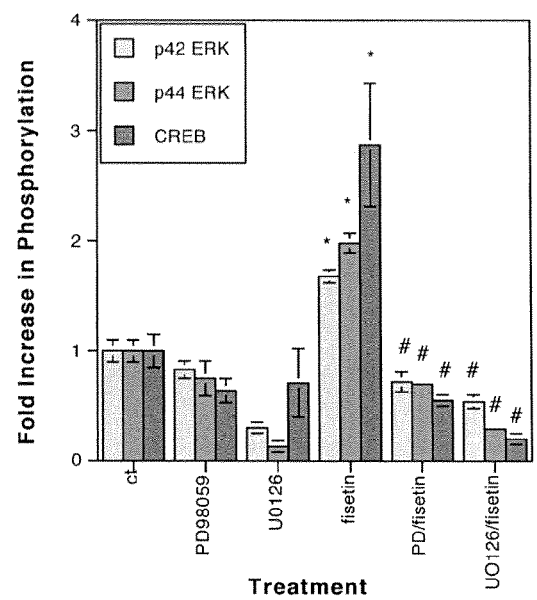

Five (5) day old cortical cultures were treated with 10 μM fisetin for 30 minutes to 6 hours; then, equal amounts of protein were analyzed by SDS-PAGE and immunoblotting with antibodies to phospho-ERK and phospho-CREB along with antibodies to the unphosphorylated forms of the proteins, which were used to demonstrate no changes in overall protein levels. The average phosphoprotein signal from the blots was quantified by densitometry and normalized to total protein, As shown in FIGS. 5A and 5B, 10 μM fisetin induced ERK activation in primary cortical neurons with a time course very similar to what was seen in PC12 cells (see FIG. 1A). In addition, fisetin treatment enhanced CREB activation in cortical neurons with a time course which was similar to that seen for ERK activation (FIGS. 5A and 5B).

Five (5) day old cortical cultures were next pretreated with 50 μM of the MEK inhibitor, PD98059, before the addition of 10 μM fisetin for 4 hours. The activation of both ERK and CREB by fisetin was blocked by PD98059 (see lane marked "PD/fis" as compared to lane marked "fis"), which indicated that CRFB activation was downstream of ERK (see FIGS. 5C and 5D).

Example 6

Fisetin Induces Long-Term Potentiation in Hippocampal Slices

Having demonstrated that fisetin affects FRK and CREB activation in cortical neurons and in view of the possible association between FRK and CREB activation and memory (Sweatt, *Curr. Opin. Neurobiol.*, 14:311-7, 2004; Carlezon et al., *Trends Neurosci.*, 28:436-45, 2005), this Example takes the next step to illustrate that fisetin affects long-term potentiation (LTP) in hippocampal slices. LTP is considered to be a good model of how memory is formed at the cellular level (Bliss and Collingridge, *Nature*, 361:31-9, 1993).

Figure 6:
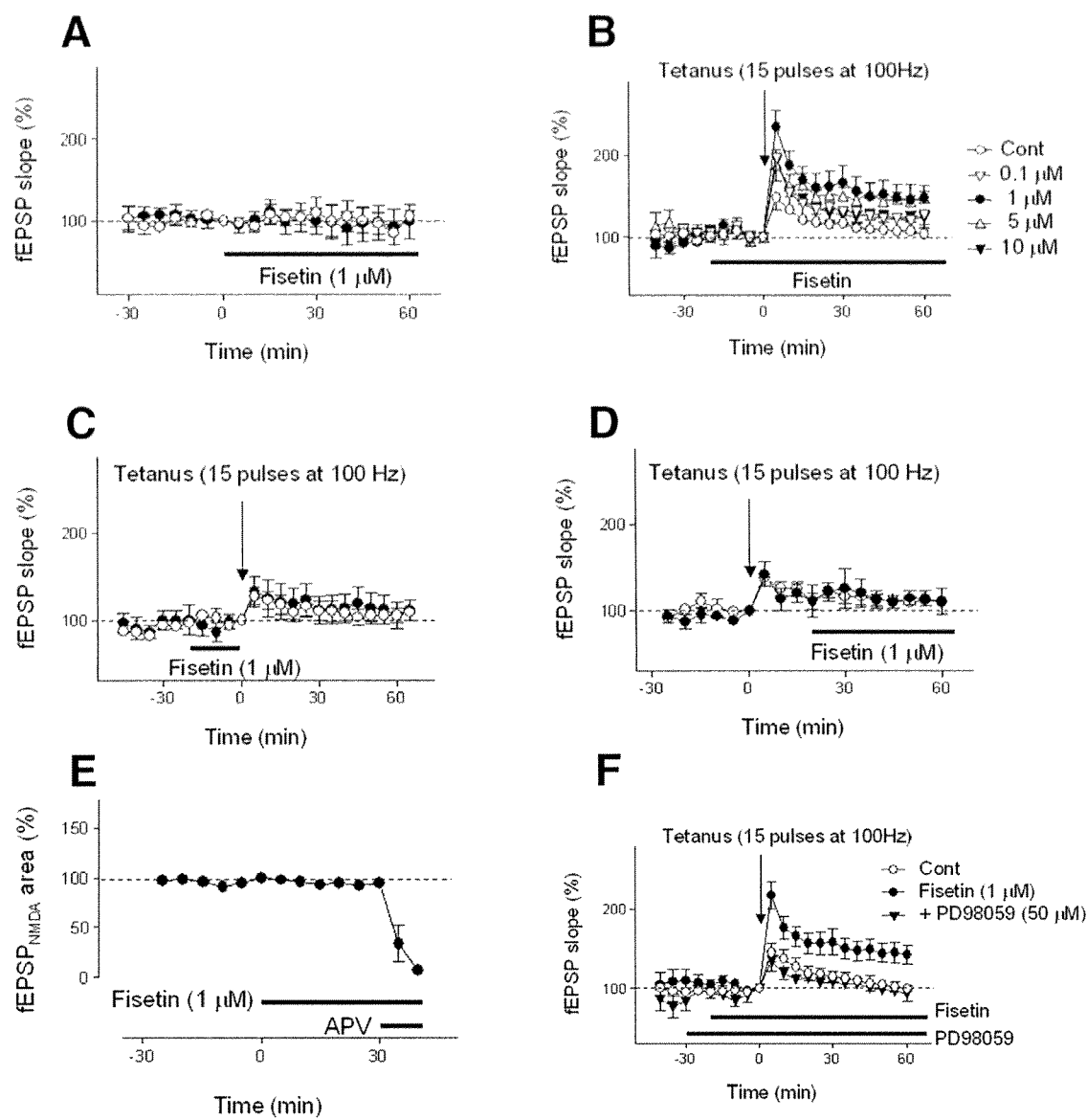
FIG. 6 is a series of graphs demonstrating that fisetin facilitates the induction of LTP following a weak tetanus in the CA1 area of rat hippocampal slices in all ERK-dependent manner. Administration of a tetanus stimulus of 15 pulses at 100 Hz is indicated by a downward arrow (panels B, C, D, and F). A period of incubation of the hippocampal slices with fisetin (panels A-F), APV (panel E) or PD98059 (panel F) is shown by solid line parallel to the x-axis.

Rat hippocampal slices were treated with fisetin for various intervals in the presence or absence of weak tetanic stimulation (15 pulses at 100 Hz). As shown in FIG. 6A, an approximately 60 minute incubation in fisetin had no direct effect on basal synaptic transmission in the CA1 area of rat hippocampal slices. A weak tetanic stimulation (15 pulses at 100 Hz) did not induce LTP in hippocampal slices; however, LTP was induced in slices incubated in fisetin for 20 minutes prior to, during and for at least 60 minutes after weak tetanic stimulation (15 pulses at 100 Hz) (see FIG. 6B). The facilitation of LTP induction by fisetin was dose dependent with a maximal effective dose of 1 μM and persisted for at least 60 minutes (FIG. 6B).

As shown in FIGS. 6C and 6D, fisetin needed to be present during the period of tetanic stimulation in order to fully promote the induction of LTP. Fisetin had no effect on aminophosphonovateric acid (APV)-dependent inhibition of excitatory postsynaptic potentials (FIG. 6E). LTP can be induced by activation of NMDA receptors, which activation is blocked by APV, ERK and CREB activation are downstream of NMDA receptor activation; thus, the results obtained with fisetin in the presence of APV are consistent with the effects of fisetin on ERK and CREB. Furthermore, the MEK inhibitor PD98059 (added 10 minutes prior to the addition of fisetin), blocked fisetin-induced facilitation of LTP, indicating a requirement for ERK activation in this process (FIG. 6F). PD98059 by itself had no effect on basal synaptic transmission.

In summary, this Example demonstrates that fisetin facilitates the induction of LTP in the CA1 area of rat hippocampal slices in an ERK-dependent manner.

Example 7

Fisetin and its Derivative Enhances Memory In Vivo

This Example illustrates that the in vitro effects of fisetin and its derivatives, e.g., as seen in differentiation assays, neuroprotection assays, and in primary cortical neurons and hippocampal slices, translate into memory enhancement in vivo.

The effect of fisetin, 3,3',4'-THF, and apigenin (5,7,4'-THF) on memory was tested in mice using an object recognition task (Ennaceur and Delacour, *Behav. Brain Res.*, 31:47-59, 1988). Among the alternatives available for testing memory, this assay has proven very effective for measuring CREB-dependent functions (Prickaerts et al., *Neurosci.*, 113: 351-61, 2002; Bourtchouladze et al., *Proc. Natl. Acad. Sci. USA*, 100:10518-22, 2003). In this test, mice are presented with two identical objects during the training period which they explore for a fixed time period. To test for memory, mice are presented one day later with two different objects, one of which was presented previously during the training and is thus familiar to the mice, and the other that is novel. The better a mouse remembers the familiar object, the more time it will spend exploring the novel object. To test the effects of fisetin, 3,3',4'-THF, or apigenin (5,7,4'-THF) in this memory task, the respective compound was administered orally to the mice before the start of the training period. Rolipram, a phosphodiesterase inhibitor that potentiates memory in this assay (Bourtchouladze et al., *Proc. Natl. Acad. Sci. USA*, 100:10518-22, 2003), requires intraperitoneal injection and was used as a positive control.

Figure 7:
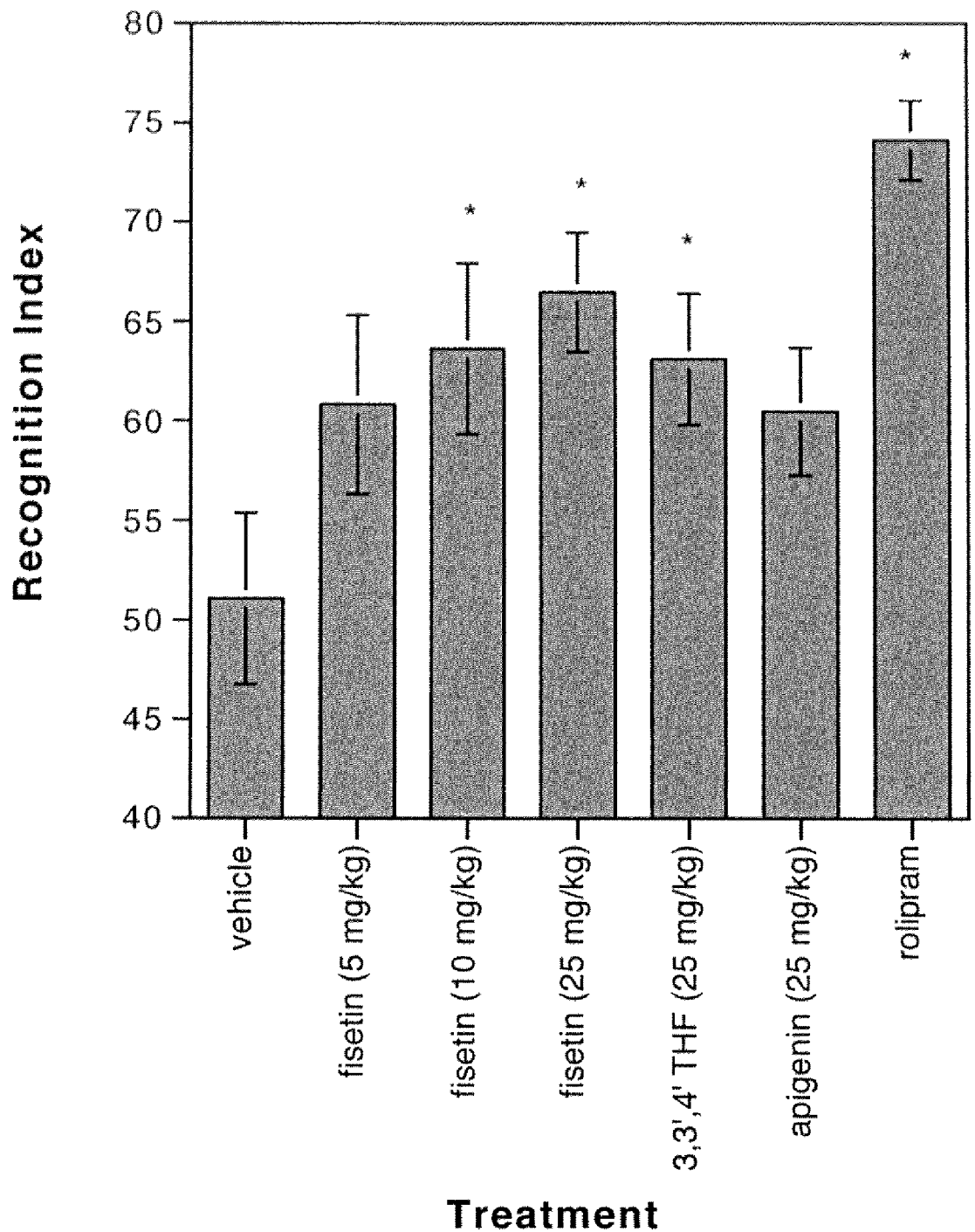
FIG. 7 is a bar graph showing the indicated oral doses of fisetin, 3,3'4'-THF, or apigenin on object recognition over a 10 minute test period. Rolipram, injected intraperitoneally at 0.1 mg/kg, served as a positive control. Data represent the mean±SEM of 10 mice/treatment group. Data were analyzed by one-way ANOVA followed by post-hoc comparisons with Fisher's test. * indicates significantly different from vehicle control (p<0.02). Similar results were obtained in 2 independent, blinded experiments.

As shown in FIG. 7, fisetin increased object recognition in a dose-dependent manner with significant effects seen at both 10 and 25 mg/kg Similarly, mice treated with 3,3',4'-THF (25 mg/kg) exhibited significantly increased object recognition. In contrast, mice treated with the S-hydroxy flavonoid apigenin, did not exhibit significantly better object recognition than mice treated with vehicle alone.

Example 8

Additional Representative Materials and Methods

This Example provides representative materials and methods useful to obtain the results described in Examples 5-7.

A. Immunoblotting

Primary cultures of rat cortical neurons were prepared as previously described by Li et al. (Neuron, 19:453-63, 1997, herein incorporated by reference as to the method). Analysis of ERK and CREB phosphorylation was performed using SDS-polyacrylamide gel electrophoresis and immunoblotting as previously described by Sagara et al. (J. Neurochem., 90:1144-1155, 2004) using equal amounts of protein from 5 day old cortical cultures. Blots were scanned and quantified using NIH Image. Results were analyzed using an unpaired Student's t-test.

B. LTP Experiments

Slice preparation and field potential recording were made as previously described by Abe and Kimura (J. Neurosci., 16:1066-71, 1996). Briefly, hippocampal slices (400 µm) were prepared from male Wistar rats (5-7 weeks old) and maintained in a chamber at 30° C., where they were continuously perfused with artificial CSF (ACSF) consisting of: 124 mM NaCl, 3.0 mM KCl, 2.2 mM $CaCl_2$, 1.4 mM $MgSO_4$, 1.24 mM $KH_2PO_4$, 25.0 mM $NaHCO_3$, and mM glucose, bubbled with 95% $O_2$/5% $CO_2$. A bipolar stimulating electrode was placed in the stratum radiatum in the CA1/CA2 border region, and the evoked field excitatory postsynaptic potentials (fEPSPs) were recorded from the stratum radiatum. The stimulus intensity was adjusted in the range of 25-55 µA to evoke fEPSPs of 50% of the maximum amplitude. Tetanic stimulation was applied at the same intensity with the test stimulation. The rising slope of fEPSP was measured as an index of synaptic efficacy. NMDA receptor-mediated synaptic responses were recorded in $Mg^{2+}$-free ACSF supplemented with 20 µM 6-cyano-7-nitroquinoxaline-2,3-dione, a non-NMDA receptor antagonist, and 50 µM picrotoxin, a $GABA_A$ receptor channel blocker. The area of field potentials recorded in this condition was measured as an index of NMDA receptor-mediated synaptic responses. All results are presented as the mean SEM of 5-12 experiments. Data were analyzed by one-way ANOVA followed by Tukey's test or Dunnett's test.

C. Object Recognition

Male C57Bl/6J mice (Jackson Laboratories) were used and the testing was done by PsychoGenics (Tarrytown, N.Y.). All mice were acclimated to the colony room for at least 2 weeks prior to testing and were tested at an average age of 8 weeks. Mice were randomly assigned across treatment groups with 10 mice in each group. For each dose tested, a 10× solution of fisetin was prepared in 95% ethanol and then diluted with 4 volumes polyethylene glycol 660 hydroxystearate (Solut HS15 from BASF) and 5 volumes phosphate buffered saline. The vehicle was contained the identical ratios of ethanol, Solut HS15 and phosphate buffered saline. All were administered orally 60 minutes prior to training at a volume of 10 ml/kg body weight. Rolipram was dissolved in 10% DMSO and administered intraperitoneally 20 minutes prior to training. The test was performed as previously described by Bourtchouladze et al. (Proc. Natl. Acad. Sci. USA, 100:10518-22, 2003). Briefly, on Day 1 mice were habituated to a circular open field arena for one hour in cage groups of four. Twenty-four (24) hours later, individual mice were placed back in the same arena which now contained two identical objects for a 15 minutes training trial. On Day 3, vehicle-, fisetin- or rolipram-treated mice were individually placed back in the same arena in the presence of both the familiar object (i.e. previously explored) and a novel object. The spatial positions of the objects were counter-balanced between subjects. Each animal's test trial was recorded and the first 10 minutes of each session were scored. Object recognition was computed using the formula: Time spent with novel object×100)/Total time spent exploring both objects. Data were analyzed by a one-way ANOVA followed by post-hoc comparisons with Fisher's test. Similar results were obtained in two independent experiments.

Example 9

Fisetin Improves Neurological Outcome in Subjects with Brain Ischemia

This Example demonstrates that fisetin improves the neurological outcome in subjects with brain ischemia.

Rabbits were embolized with small blood clots of varying size (from about 1 mg to about 4 mg) according to the procedure described by Lapchak et al. (Exp. Neurol., 188.279-285, 2004). The clot dose administered has been shown to be proportional to the severity of brain ischemia experienced by the subject (Lapchak et al., Exp. Neurot., 188:279-285, 2004). In some subjects, fisetin treatment (50 mg/kg delivered intravenously) was given as a bolus 5 minutes after embolization. Twenty four (24) hours later, a naïve observer rated each treated or control animal as either behaviorally normal or abnormal. Rabbits judged "abnormal" included those with at least one of the following symptoms: ataxia, leaning, circling, lethargy, nystagmus, loss of balance, loss of sensation and occasionally paraplegia. The number of animals exhibiting behavioral deficits for each clot weight (in mg) was determined. The effective stroke dose or P50 value was then calculated as the amount of microclots (in mg) that produce behavioral impairment in 50% of the animals within a specific treatment group.

Figure 8:
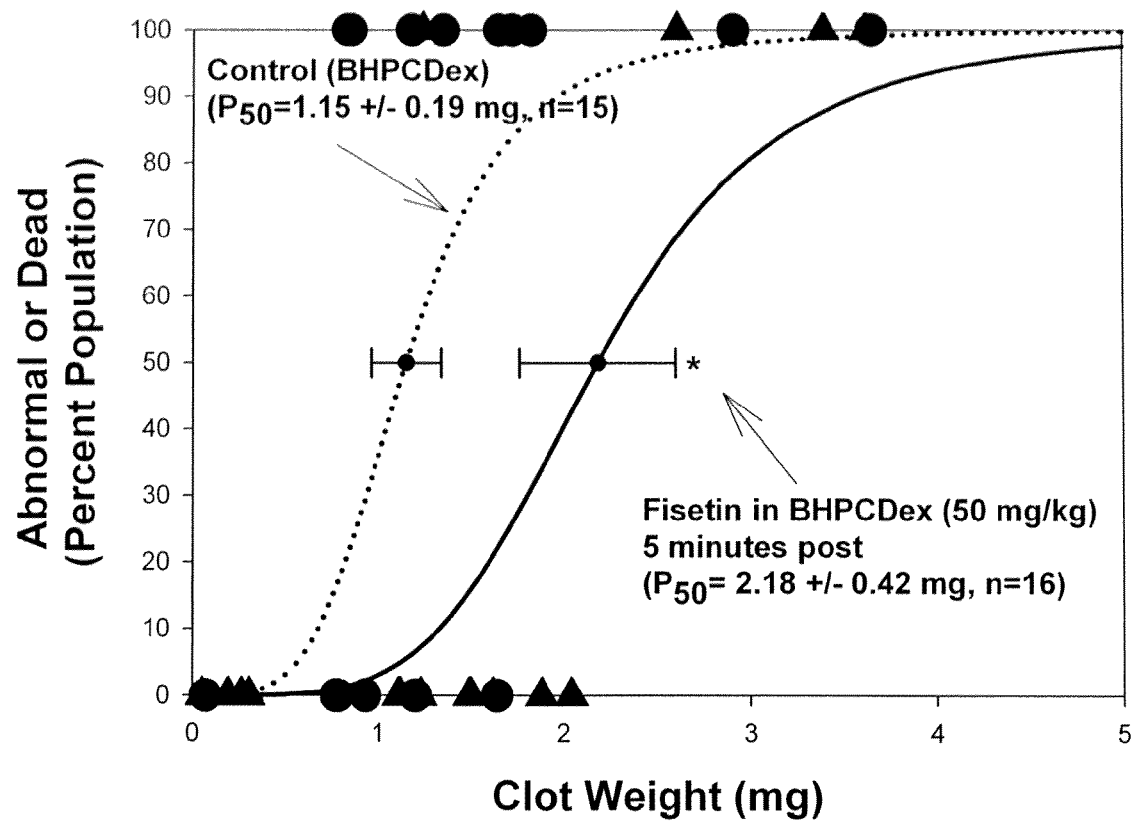
FIG. 8 shows dead or functionally impaired subjects as a function the weight (mg) of blood clots administered to the subjects. Control subjects (receiving no fisetin treatment) are shown by closed circles and fisetin-treated subjects are shown by closed triangles. The curves relating to control and treated subjects are shown by dotted and solid lines, respectively.

As shown in FIG. 8, subjects that did not receive fisetin post-embolism exhibited functional deficits even when the size of the delivered clot was relatively small. The P50 value (mg clot that produce behavioral deficits in 50% of the animals measured 24 hours post-embolism) for control subjects was 1.15±0.19 mg (n=15). Fisetin treatment increased the P50 value to 2.18±0.42 mg (n=16).

In summary, fisetin has a protective effect when delivered in vivo to a subject at substantial risk for neurological impairment as a result of brain ischemia. Fisetin derivatives (e.g., 5-desoxy-flavones and 5-desoxy-flavonols and as otherwise described throughout this disclosure) are expected to have a similar outcome.

Example 10

Fisetin Prevents MPTP-Induced Striatal Dopamine Loss

This Example demonstrates that fisetin prevents dopamine loss in an in vivo model of Parkinson's disease. Dopamine loss is correlated with symptoms of Parkinson's disease, including memory impairment.

C57BL/6 mice from about 11 to 12 week old (20-25 g) were injected with a single dose of 3-1 mg/kg 1-methyl-4-phenyl-1,2,3,6-tetrahydropyridine (MPTP). MPTP is toxic to dopaminergic neurons in the substantia nigra, and produces many of the symptoms of Parkinson's disease. MPTP-treated mice have long been used as a model of human Parkinson's disease (see, e.g., reviews by Smeyne and Jackson-Lewis, Brain Bes. Mol. Brain Res., 134(1):57-66, 2005; Tetrud and Langston, *Acta Neurol. Scand. Suppl.*, 126:35-40, 1989). After 8 days, the animals were euthanized and the striata dissected and assayed for dopamine content by HPLC combined with electrochemical detection, as previously described (Irwin e/al., *Brain Res.*, 572:224-231, 1992). One group of untreated mice (n=4) and one group of MPTP-treated mice (n=4) received orally administered fisetin (25 mg/kg) beginning one day before treatment groups received MPTP and continuing for the same time period as MPTP treatment in treatment groups. Mice untreated with MPTP or fisetin (control) and mice treated with MPTP alone were also examined.

Figure 9:
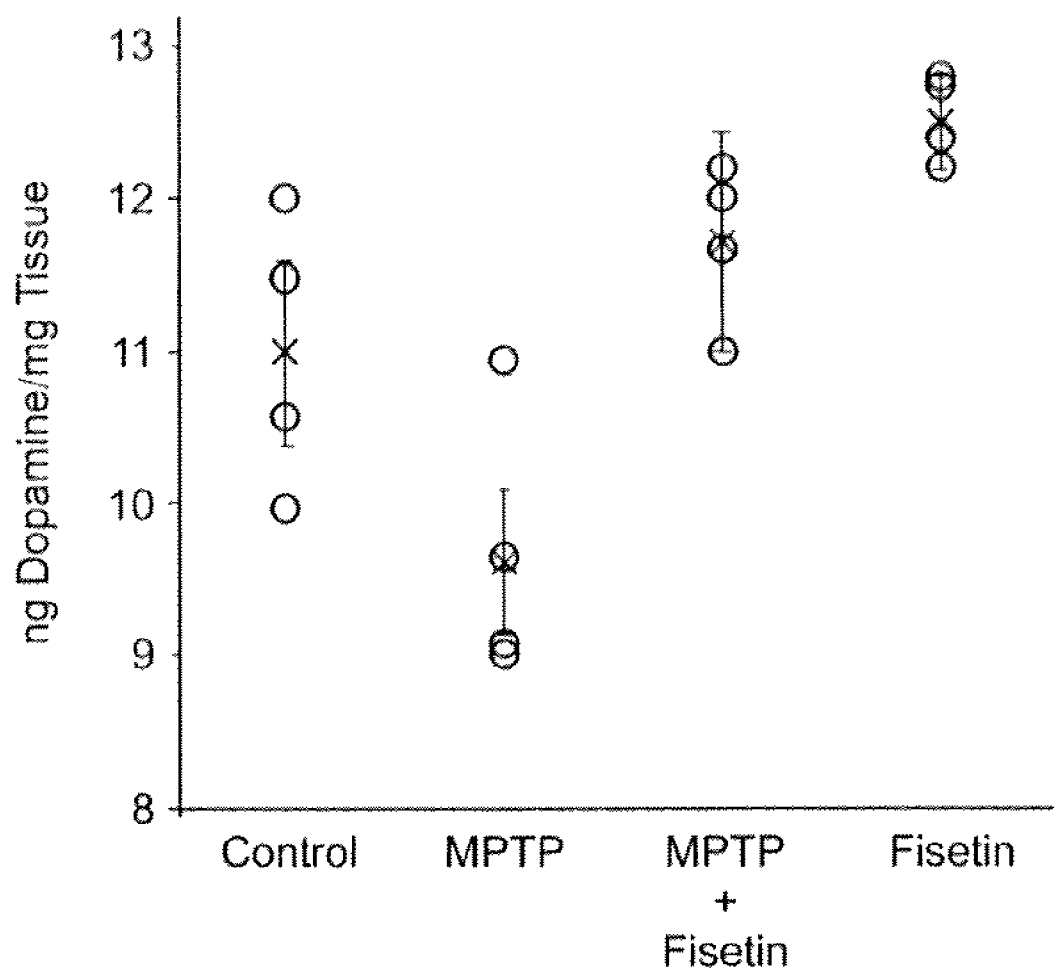
FIG. 9 shows the concentration (ng/gm tissue) of dopamine in the striata (open circles) of untreated (control) subjects or subjects treated with MPTP alone, MPTP and fisetin, or fisetin alone. In each treatment group, the "x" indicates the average value for the group.

As shown in FIG. 9, the concentration of dopamine (ng/mg tissue) in striata of MPTP-treated mice was lower than all other groups examined. Mice treated with both MPTP and fisetin had striatal dopamine concentrations at least as high as control (untreated) mice. Mice treated with fisetin alone had the highest concentrations of striatal dopamine.

In summary, this Example indicates another in vivo application for the use of fisetin in the treatment of memory-impairing disease, such as Parkinson's disease. Fisetin derivatives (e.g., 5-desoxy-flavones and 5-desoxy-flavonols and as otherwise described throughout this disclosure) are expected to have a similar outcome.

Example 11

Fisetin Activates ERK and CREB in Hippocampal Slices

This example describes methods used to demonstrate that in addition to PC12 cells and primary neuronal cultures, fisetin promotes ERK activation in hippocampal slices.

Hippocampal slices in artificial cerebral spinal fluid (ACSF) were treated with either 1 μM fisetin for 5-20 minutes or pretreated for 30 minutes with either 50 μM PD98059 (PD) or 10 μM U0126 (J) before the addition of 1 μM fisetin for 5 minutes. Equal amounts of protein were analyzed by SDS-PAGE and immunoblotting with antibodies to phospho-ERK and phospho-CRFB along with antibodies to the unphosphorylated forms of the proteins. The average phosphoprotein signal from the blots was quantified by densitometry and normalized to total protein was plotted±S.D.

As shown in FIG. 10A, 1 μM fisetin induced rapid activation of both ERK1 (p44) and ERK2 (p42) within 5 minutes of treatment, which was sustained at a lower level for up to 20 minutes (FIGS. 10A and 10C). The 2-fold increase in ERK 1 and ERK2 phosphorylation observed following treatment of the hippocampal slices with fisetin is very similar to the increases in ERK phosphorylation reported following treatment of slices with either glutamate (1.5-2-fold) (Vanhoutte et al., *Mol. Cell. Biol.* 19:136-46, 1999) or NMDA (~2.5-fold) (English & Sweatt, *J. Biol. Chem.* 272:19103-6, 1997).

One of the key signaling molecules activated downstream of ERK which is involved in learning and memory is the transcription factor cAMP-response-element binding protein (CREB) (Tully et al., *Nat. Rev. Drug Discov.* 2:267-77, 2003; Carlezon, et al., *Trends Neurosci.* 28:436-45, 2005). CREB, in turn, regulates a transcription factor cascade that eventually results in the facilitation of memory. Fisetin treatment of hippocampal slices enhances CREB activation with a time course which is similar to that seen for ERK activation (FIGS. 10A and 10C). The ~3-fold increase in CREB phosphorylation seen following the treatment of the hippocampal slices with fisetin is very similar to the increase in CREB phosphorylation reported following treatment of slices with glutamate (~2.5-fold) (Vanhoutte et al., *Mol. Cell. Biol.* 19:136-46, 1999).

The activation of both ERK and CREB by fisetin is blocked by pretreatment with the MEK inhibitors PD98059 and U0126, indicating that CREB activation is downstream of ERK activation (FIGS. 10B and D).

Example 12

Fisetin is not a Phosphodisterase Inhibitor

This example describes methods used to demonstrate that fisetin works through a mechanism distinct to that of rolipram. To date, phosphodiesterase 4 (PDE4) inhibitors such as rolipram are the only compounds that have been shown to both increase CREB phosphorylation and enhance memory (Tully et al., *Nat. Rev. Drug Discov.* 2:267-77, 2003). These PDE4 inhibitors activate C(RFB by increasing the levels of the CRFB activator, cAMP, through inhibition of its breakdown.

Hippocampal slices were treated with fisetin using the conditions where maximal stimulation of CREB phosphorylation and facilitation of LTP were observed. Briefly, hippocampal slices in ACSF were treated with 1 μM fisetin for 5 minutes (fisetin) or 3 μM rolipram for 30 minutes (rolipram) and then either immediately frozen or treated with 5 pIM forskolin for an additional 15 minutes (rolipram+forskolin; fisetin+forskolin) prior to freezing. Additional slices were treated only with 5 μM forskolin for 15 minutes (forskolin). Forskolin, an activator of adenylyl cyclase, and rolipram were used as positive controls. The levels of cAMP in the slices were measured using a Scintillation Proximity Assay and presented as pmole/mg protein±S.D.

Figure 11:
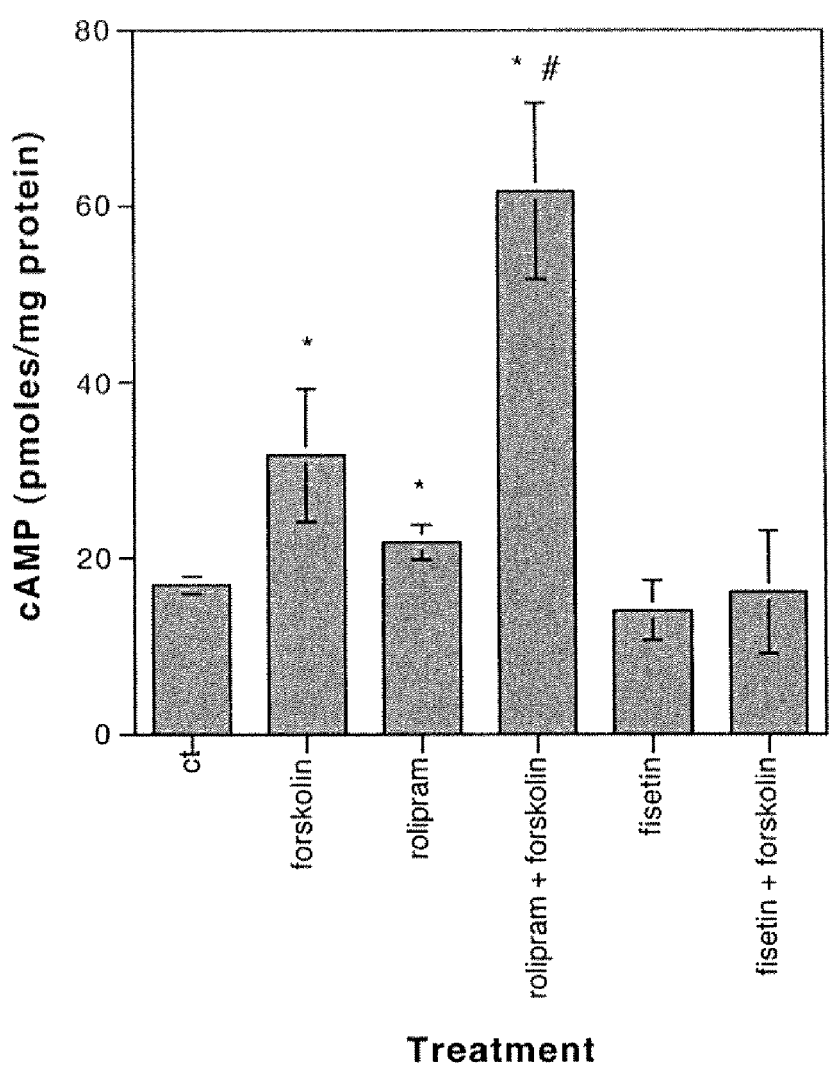
FIG. 11 is a bar graph showing that fisetin does not increase cAMP levels in hippocampal slices and works through a mechanism distinct to that of rolipram. * indicates significantly different from control (P<0.05), # indicates significantly different from forskolin or rolipram alone (P<0.005).

As shown in FIG. 11, and in agreement with published data (Barad et al., *Proc. Natl. Acad. Sci. USA* 95:15020-15, 1998), 3 μM rolipram alone modestly increased cAMP levels in the slices and significantly potentiated the effect of forskolin on cAMP levels. In contrast, fisetin had no effect on cAMP levels by itself nor did it potentiate the effect of forskolin. These data are consistent with earlier results obtained using PC12 cells showing that fisetin treatment does not result in the activation of the cAMP target protein kinase A (Sagara et al., *J. Neurochem.* 90:1144-55, 2004) and indicate that fisetin activates CREB through a mechanism that is distinct from that of rolipram.

Example 13

Oral Administration of Fisetin Enhances Memory In Vivo

This example describes use of the Morris water maze (MWM) to examine hippocampus-dependent spatial learning and memory in rats. The standard test consists of two parts; a training phase, which measures the ability of the animals to learn where a hidden platform is located within an opaque pool of water and a probe test, which is performed 24 hours after the last training trial and measures the ability of the animals to remember the location of the platform (Vorhees & Williams, *Nature Protocols* 1.848-58, 2(006))

To test whether oral administration of fisetin could increase spatial learning and/or memory, young male Sprague-Drawley rats (8 weeks old) were administered fisetin by gavage (25 mg/kg) beginning one day before the training phase and continuing throughout the 8 days of training. The rats were given four trials a day for 8 days. Retention of the spatial training was assessed 24 hours after the last training trial. The probe trial consisted of a 60 second free swim in the pool without the platform. Both the training and probe trials were monitored by a video camera mounted above the pool and all data were analyzed by software provided with the video-tracking program. Fisetin had no significant effect on either swim speed or thigmotaxis.

Figure 12:
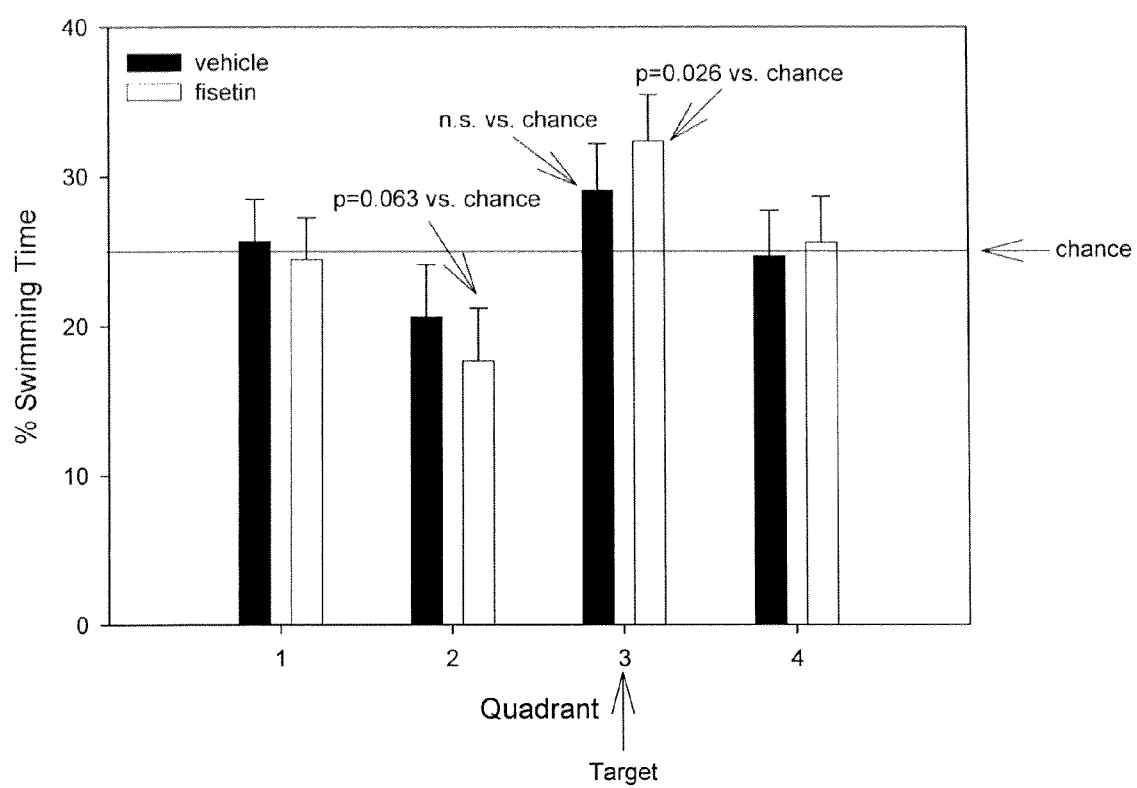
FIG. 12 is a bar graph showing that fisetin enhances spatial memory in rats.

Although there was no clear effect of fisetin on the ability of the rats to learn the location of the hidden platform, there was a significant effect of fisetin on the ability of the rats to remember where the platform was located (FIG. 12). Thus, during the probe test, the fisetin-treated rats spent significantly more time in the quadrant of the pool where the platform had been located, as compared to the vehicle-treated rats, indicating that fisetin administration increases spatial memory. This result is consistent with the fisetin-induced enhancement of long-term memory observed in mice using the object discrimination test (see Example 7 and FIG. 7).

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method for enhancing memory in a normal subject consisting of administering to the subject an effective amount of a 5-desoxy-flavone or 5-desoxy-flavonol or pharmaceutically acceptable salt of either thereof, thereby enhancing memory in the subject.

2. The method of claim 1, wherein the 5-desoxy-flavone is a 5(H)-flavone and the 5-desoxy-flavonol is 5(H)-flavonol.

3. The method of claim 1, wherein the 5-desoxy-flavone or the 5-desoxy-flavonol is a compound having the formula:

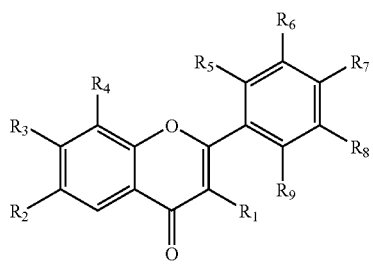

wherein:
$R_1$, $R_2$, $R_3$, $R_4$, $R_5$, $R_6$, $R_7$, $R_8$, and $R_9$ are independently hydrogen, alkyl, hydroxyl, acyl, acyloxy, alkoxy carbonyl or alkoxy;
at least one of $R_6$ and $R_7$ is hydroxyl, acyl, or acyloxy; and
at least two of $R_1$, $R_3$, $R_6$, and $R_7$ are hydroxyl, acyl, or acyloxy;
or a pharmaceutically acceptable salt thereof.

4. The method of claim 3, wherein $R_1$, $R_2$, $R_3$, $R_4$, $R_5$, $R_6$, $R_7$, $R_8$, and $R_9$ are independently hydrogen, hydroxyl, acyl, alkoxy carbonyl or acyloxy.

5. The method of claim 3, wherein $R_1$, $R_2$, $R_3$, $R_4$, $R_5$, $R_6$, $R_7$, $R_8$, and $R_9$ are independently hydrogen, hydroxyl, or acyl; at least one of $R_6$ and $R_7$ is hydroxyl, or acyloxy; and at least two of $R_1$, $R_3$, $R_6$, and $R_7$ are hydroxyl, or acyloxy.

6. The method of claim 1, wherein the 5-desoxy-flavone or the 5-desoxy-flavonol is a compound having the formula:

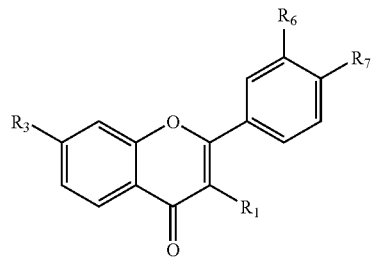

wherein:
$R_1$, $R_3$, $R_6$, and $R_7$ are independently hydrogen, alkyl, hydroxyl, acyl, acyloxy, alkoxy carbonyl or alkoxy;
at least one of $R_6$ and $R_7$ is hydroxyl, acyl, alkoxy carbonyl or acyloxy; and
at least two of $R_1$, $R_3$, $R_6$, and $R_7$ are hydroxyl, acyl, alkoxy carbonyl or acyloxy;
or a pharmaceutically acceptable salt thereof.

7. The method of claim 6, wherein $R_1$, $R_3$, $R_6$, and $R_7$ are independently hydrogen, hydroxyl, acyl, alkoxy carbonyl or acyloxy.

8. The method of claim 6, wherein $R_1$, $R_3$, $R_6$, and $R_7$ are independently hydrogen, hydroxyl, or acyl; at least one of $R_6$ and $R_7$ is hydroxyl, or acyloxy; and at least two of $R_1$, $R_3$, $R_6$, and $R_7$ are hydroxyl, or acyloxy.

9. The method of claim 3, wherein $R_6$ is hydroxyl.

10. The method of claim 3, wherein $R_7$ is hydroxyl.

11. The method of claim 3, wherein $R_6$ and $R_7$ are hydroxyl.

12. The method of claim 3, wherein $R_1$ and $R_6$ are hydroxyl.

13. The method of claim 3, wherein $R_1$ and $R_7$ are hydroxyl.

14. The method of claim 3, wherein $R_1$, $R_6$, and $R_7$ are hydroxyl.

15. The method of claim 3, wherein $R_3$, $R_6$, and $R_7$ are hydroxyl.

16. The method of claim 3, wherein $R_1$, $R_3$, and $R_6$, are hydroxyl.

17. The method of claim 3, wherein $R_1$, and $R_3$, and $R_7$ are hydroxyl.

18. The method of claim 3, wherein alkoxy is lower alkoxy.

19. The method of claim 18, wherein lower alkoxy is methoxy.

20. The method of claim 3, wherein acyloxy is lower acyloxy.

21. The method of claim 3, wherein alkyl is lower alkyl.

22. The method of claim 21, wherein lower alkyl is methyl or ethyl.

23. The method of claim 1, wherein the 5-desoxy-flavone or 5-desoxy-flavonol is 3,3',4',7-tetrahydroxyflavone (fisetin), 3,3',4'-trihydroxyflavone, 3',4',7-trihydroxyflavone, 3,3',7-trihydroxyflavone, 3,4',7-trihydroxyflavone, 3,3'-dihydroxyflavone, 3,4'-dihydroxyflavone, or 3',4'-dihydroxyflavone.

24. The method of claim 1, wherein the compound 5-desoxy-flavonol is 3,3',4',7-tetrahydroxyflavone (fisetin), 3,3',4'-trihydroxyflavone, or 3,4',7-trihydroxyflavone.

25. The method of claim 1, wherein the 5-desoxy-flavonol is 3,3',4'-trihydroxyflavone.

26. The method of claim 1, wherein the 5-desoxy-flavonol is not 3,3',4',7-tetrahydroxyflavone (fisetin).

27. The method of claim 1, wherein the effective amount of the 5-desoxy-flavone or 5-desoxy-flavonol is from about 50 mg to about 1000 mg.

28. A method for enhancing memory in a normal subject consisting of administering to the subject an effective amount of a 5-desoxy-flavone or 5-desoxy-flavonol or pharmaceutically acceptable salt of either thereof, in combination with an effective amount of one or more of vinpocetine, piracetam, or one or more antioxidants, thereby enhancing memory in the subject.

29. The method of claim 28, wherein the 5-desoxy-flavonol is 3,3',4',7-tetrahydroxyflavone (fisetin), 3,3',4'-trihydroxyflavone, or 3,4',7-trihydroxyflavone.

30. The method of claim 29, wherein the 5-desoxy-flavonol is 3,3',4',7-tetrahydroxyflavone (fisetin).

31. The method of claim 28, wherein the method consists of administering to the subject an effective amount of a 5-desoxy-flavone or 5-desoxy-flavonol or pharmaceutically acceptable salt of either thereof, in combination with an effective amount of vinpocetine, thereby enhancing memory in the subject.

32. The method of claim 28, wherein the method consists of administering to the subject an effective amount of a 5-desoxy-flavone or 5-desoxy-flavonol or pharmaceutically acceptable salt of either thereof, in combination with an effective amount of piracetam, thereby enhancing memory in the subject.

33. The method of claim 28, wherein the method consists of administering to the subject an effective amount of a 5-desoxy-flavone or 5-desoxy-flavonol or pharmaceutically acceptable salt of either thereof, in combination with an effective amount of one or more antioxidants, thereby enhancing memory in the subject.

34. The method of claim 30, wherein the method consists of administering to the subject an effective amount of fisetin in combination with an effective amount of vinpocetine, thereby enhancing memory in the subject.

35. The method of claim 30, wherein the method consists of administering to the subject an effective amount of fisetin in combination with an effective amount of piracetam, thereby enhancing memory in the subject.

36. The method of claim 30, wherein the method consists of administering to the subject an effective amount of fisetin in combination with an effective amount of one or more antioxidants, thereby enhancing memory in the subject.

37. The method of claim 36, wherein the one or more antioxidants is selected from the group consisting of Vitamin C, Vitamin E, alpha-carotene, beta-carotene, Coenzyme Q, selenium, zinc, manganese, lycopene, lutein, zeaxanthin, and astaxanthin.

38. The method of claim 30, wherein the method consists of administering to the subject an effective amount of fisetin in combination with an effective amount of vinpocetine, piracetam and one or more antioxidants, thereby enhancing memory in the subject.

* * * * *